United States Patent
Hirose

(10) Patent No.: US 10,898,290 B2
(45) Date of Patent: Jan. 26, 2021

(54) SURGICAL MICROSCOPE DEVICE AND SURGICAL MICROSCOPE SYSTEM

(71) Applicant: Sony Olympus Medical Solutions Inc., Tokyo (JP)

(72) Inventor: Kenji Hirose, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 86 days.

(21) Appl. No.: 15/736,634

(22) PCT Filed: Jun. 16, 2016

(86) PCT No.: PCT/JP2016/067937
§ 371 (c)(1),
(2) Date: Dec. 14, 2017

(87) PCT Pub. No.: WO2016/208485
PCT Pub. Date: Dec. 29, 2016

(65) Prior Publication Data
US 2018/0168767 A1 Jun. 21, 2018

(30) Foreign Application Priority Data

Jun. 26, 2015 (JP) .................................. 2015-128853

(51) Int. Cl.
*A61B 90/25* (2016.01)
*G02B 7/00* (2006.01)
(Continued)

(52) U.S. Cl.
CPC .............. *A61B 90/25* (2016.02); *G02B 7/001* (2013.01); *G02B 21/0012* (2013.01);
(Continued)

(58) Field of Classification Search
CPC ... A61B 90/20; A61B 90/25; A61B 2090/373; A61B 2090/50; A61B 2090/5025;
(Continued)

(56) References Cited

U.S. PATENT DOCUMENTS 5,288,043 A   2/1994 Tigliev
6,514,239 B2  2/2003 Shimmura et al.
(Continued)

FOREIGN PATENT DOCUMENTS

CN    1925809 A    3/2007
CN    102858225 A  1/2013
(Continued)

OTHER PUBLICATIONS

OPMI Pentero 900 Surgical Microscope, Technical Data, https://www.zeiss.com/meditec/us/products/plastic-reconstructive-surgery/surgical-microscopes/opmi-pentero-900.html#technical-data, accessed online on Sep. 5, 2019 (Year: 2019).*

(Continued)

*Primary Examiner* — Stephone B Allen
*Assistant Examiner* — Adam W Booher
(74) *Attorney, Agent, or Firm* — Xsensus, LLP

(57) ABSTRACT

A surgical electronic microscope device (10) includes a microscope unit (110) and a support unit (120) that supports the microscope unit (110). The microscope unit (110) images an operative site of a patient (330) on an operating table (340), and outputs an image signal. The support unit (120) includes a prop unit (290*c*). The prop unit (290*c*) supports a second arm (290*b*) rotatably around an axis (05). The second arm (290*b*) supports a first arm (290*a*) rotatably around an axis (04). The first arm (290*a*) supports the microscope unit (110). Pivoting the second arm (290*b*) on the axis (05) while keeping the first arm (290*a*) substantially level makes it possible to change a height of the microscope unit (110). A (Continued)

length (V) of the second arm (290b) is greater than a length (H) of the first arm (290a). Accordingly, a movable range of the microscope unit (110) in a vertical direction is wide. Both an operation performed by a surgeon at a standing position and an operation performed by a surgeon at a seated position can be therefore covered.

10 Claims, 18 Drawing Sheets

(51) Int. Cl.
*G02B 21/00* (2006.01)
*G02B 21/24* (2006.01)
*A61B 90/00* (2016.01)
*A61B 90/50* (2016.01)
*G02B 21/36* (2006.01)

(52) U.S. Cl.
CPC ........ *G02B 21/24* (2013.01); *A61B 2090/373* (2016.02); *A61B 2090/504* (2016.02); *A61B 2090/506* (2016.02); *G02B 21/362* (2013.01); *G02B 21/368* (2013.01)

(58) Field of Classification Search
CPC ........ A61B 2090/504; A61B 2090/506; A61B 2090/508; G02B 7/001; G02B 21/0012; G02B 21/24; G02B 21/362; G02B 21/368
See application file for complete search history.

(56) References Cited

U.S. PATENT DOCUMENTS

| | | | |
|---|---|---|---|
| 8,200,073 | B1 | 6/2012 | Nakamura |
| 2001/0027313 | A1 | 10/2001 | Shimmura et al. |
| 2003/0053202 | A1 | 3/2003 | Sibata et al. |
| 2003/0151806 | A1* | 8/2003 | Schmidt ................ A61B 90/25 359/384 |
| 2006/0291044 | A1 | 12/2006 | Nozawa et al. |
| 2006/0291045 | A1 | 12/2006 | Nakamura et al. |
| 2008/0231948 | A1* | 9/2008 | Nakamura ............. A61B 90/36 359/378 |
| 2012/0296159 | A1 | 11/2012 | Kanazawa et al. |
| 2015/0297311 | A1* | 10/2015 | Tesar |

FOREIGN PATENT DOCUMENTS

| | | |
|---|---|---|
| EP | 1 721 581 A1 | 11/2006 |
| JP | 57-500702 A | 4/1982 |
| JP | 04-321008 A | 11/1992 |
| JP | 8-266555 A | 10/1996 |
| JP | 2001-258903 A | 9/2001 |
| JP | 2002-272760 A | 9/2002 |
| JP | 2005-6960 A | 1/2005 |
| WO | WO 2012/014944 A1 | 2/2012 |
| WO | 2015/042460 A1 | 3/2015 |
| WO | WO 2016/208485 A1 | 12/2016 |

OTHER PUBLICATIONS

"The Next Generation"—OPMI Pentero 900 by Carl Zeiss Meditec, published Nov. 29, 2011, https://www.youtube.com/watch?v=ucS8UounXOg, accessed online on Sep. 5, 2019 (Year: 2011).*
OPMI Pentero 900—The Next Generation, Carl Zeiss Meditec AG, Published 2011, Accessed Nov. 20, 2019, https://www.getter-biomed.co.il/wp-content/uploads/2016/10/Pentero-900.pdf (Year: 2011).*
Office Action dated Oct. 30, 2018 in Japanese Patent Application No. 2017-245781, with English translation citing documents AO therein, 7 pages.
Extended European Search Report dated Mar. 13, 2019 in corresponding European Patent Application No. 16814256.0 citing documents AA, AB and AO therein, 9 pages.
International Search Report dated Aug. 30, 2016, in PCT/JP2016/067937 filed Jun. 16, 2016.
Written Opinion of the International Searching Authority dated May 16, 2017, in PCT/JP2016/067937 filed Jun. 16, 2016.
Office Action issued in Chinese Application 2016800357321 dated Nov. 25, 2019.
Office Action dated Jun. 2, 2020 in Japanese Patent Application No. 2019-124060, 17 pages.
Surgical Operating Table DR-8800, Medical Development in Takara Belmont Corp, May 15, 2020, URL, https://www.takarabelmont.co.jp/medical/products/deyail/72, with cover page, 4 pages.

* cited by examiner

SURGICAL MICROSCOPE DEVICE AND SURGICAL MICROSCOPE SYSTEM

TECHNICAL FIELD

The present disclosure relates to a surgical microscope device and a surgical microscope system.

BACKGROUND ART

Microscope devices are traditionally used to magnify and observe operative sites in surgery such as neurosurgery, which targets minute areas. A microscope device has the microscope unit supported by an arm unit (support unit) (see, for example, Patent Literatures 1 and 2).

An operative site can be an extremely small area, so that a microscope device is required to be able to adjust the position of the microscope unit with high accuracy to allow a surgeon to observe a desired position. The support unit that supports the microscope unit is thus configured as a balance arm including a counterweight (counterbalance) in many cases as exemplified as the microscope devices described in Patent Literatures 1 and 2. The support unit configured as a balance arm allows a surgeon to move the microscope unit as if the surgeon operated the microscope unit under zero gravity, which can improve the operability of the surgeon.

CITATION LIST

Patent Literature

Patent Literature 1: JP H8-266555A
Patent Literature 1: JP 2005-6960A

DISCLOSURE OF INVENTION

Technical Problem

Here, it is an optical microscope units that is included in the microscope devices described in Patent Literatures 1 and 2. A surgeon directly looks through the ocular lens provided to the microscope unit to observe an operative site. At this time, a surgeon comes under the support unit for observation in most cases (which will be referred to as overhead style) (see, for example, FIG. 1 of Patent Literature 2). The structure of the support unit is thus designed in many cases on the assumption that the microscope device (which will also be referred to as optical microscope devices for the sake of convenience) including an optical microscope unit is used in the overhead style. Accordingly, the size of the entire device tends to increase.

Meanwhile, microscope devices have been recently developed that include an image sensor and an electronic imaging microscope unit which can electronically image an operative site. A microscope device (which will also be referred to as electronic imaging microscope device for the sake of convenience) including an electronic imaging microscope unit displays an image of an operative site captured by the microscope unit on a display device installed in an operating room, and a surgeon performs an operation while observing the image of the operative site shown on the display device.

Electronic imaging microscope units do not require any component such as an ocular lens, and are thus smaller and weight less than optical microscope units. Further, an optical microscope unit requires the ocular unit to be disposed at a position that can be accessed by a surgeon, so that the movable range required of the microscope unit is substantially limited. In contrast, a wider movable range is required of an electronic imaging microscope unit to allow the electronic imaging microscope unit to image an operative site from any direction. Moreover, with respect to an electronic imaging microscope device, a surgeon performs an operation while watching a display device. The electronic imaging microscope device requires the support unit and the microscope unit to be disposed such that the view of the surgeon observing the display device is obstructed as little as possible.

In this way, the configuration of the microscope unit, the movable range required of the support unit, the use mode, or the like of an electronic imaging microscope device are different from those of an optical microscope device. Accordingly, even if the configuration of the support unit in an optical microscope device designed on the assumption of use in the overhead style is directly applied to an electronic imaging microscope device, the configuration is not always appropriate for the electronic imaging microscope device.

The present disclosure then proposes a novel and improved surgical microscope device and surgical microscope system each of which includes a support unit more appropriate for an electronic imaging microscope device, and can hereby further improve the convenience of a surgeon.

Solution to Problem

According to the present disclosure, there is provided a surgical microscope device including: a microscope unit configured to image an operative site of a patient on an operating table, and output an image signal; and a support unit configured to support the microscope unit at a distal end. In a case where it is assumed that the support unit includes a first arm, a second arm, and a prop unit in an order from a distal-end side, the second arm supporting a proximal end of the first arm at a distal end rotatably around a first rotation axis orthogonal to a vertical direction and a front-back direction, the prop unit extending from a floor substantially in the vertical direction and supporting a proximal end of the second arm at a distal end rotatably around a second rotation axis orthogonal to the vertical direction and the front-back direction, the support unit is configured such that a length of the second arm as a length between the first rotation axis and the second rotation axis is greater than a length of the first arm as a length between the first rotation axis and an optical axis of the microscope unit disposed to have the optical axis substantially vertical.

Further, according to the present disclosure, there is provided a surgical microscope system including: a microscope device including a microscope unit configured to image an operative site of a patient on an operating table and output an image signal, and a support unit configured to support the microscope unit at a distal end; and a display device configured to display an image based on the image signal. In a case where it is assumed that the support unit includes a first arm, a second arm, and a prop unit in an order from a distal-end side, the second arm supporting a proximal end of the first arm at a distal end rotatably around a first rotation axis orthogonal to a vertical direction and a front-back direction, the prop unit extending from a floor substantially in the vertical direction and supporting a proximal end of the second arm at a distal end rotatably around a second rotation axis orthogonal to the vertical direction and the front-back direction, the support unit is configured such that a length of the second arm as a length between the first rotation axis and the second rotation axis is greater than a length of the first arm as a length between the first rotation axis and an optical axis of the microscope unit disposed to have the optical axis substantially vertical.

According to the present disclosure, a support unit of a surgical microscope device is configured such that a length of a second arm is greater than a length of a first arm. It is thus possible to secure a microscope unit a wider movable range in a vertical direction while keeping the first arm substantially level when the microscope unit images an operative site in an operation. An image of an operative site captured by the microscope unit is displayed on a display device installed in an operating room, and a surgeon performs an operation while observing the image of the operative site shown on the display device in an operation using the surgical microscope device. Keeping the first arm substantially level therefore secures the surgeon a working space and view, which can further improve the convenience of the surgeon. Further, if the microscope unit is secured a wider movable range in the vertical direction, it is possible to cover both an operation at a standing position and an operation at a seated position, at which the microscope unit has different use area heights. In other words, the surgical microscope device according to the present disclosure makes it possible to perform an operation while keeping the first arm substantially level in any case of an operation at the standing position and an operation at the seated position.

Advantageous Effects of Invention

As described above, according to the present disclosure, a support unit more appropriate for an electronic imaging microscope device is included, thereby making it possible to further improve the convenience of a surgeon. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
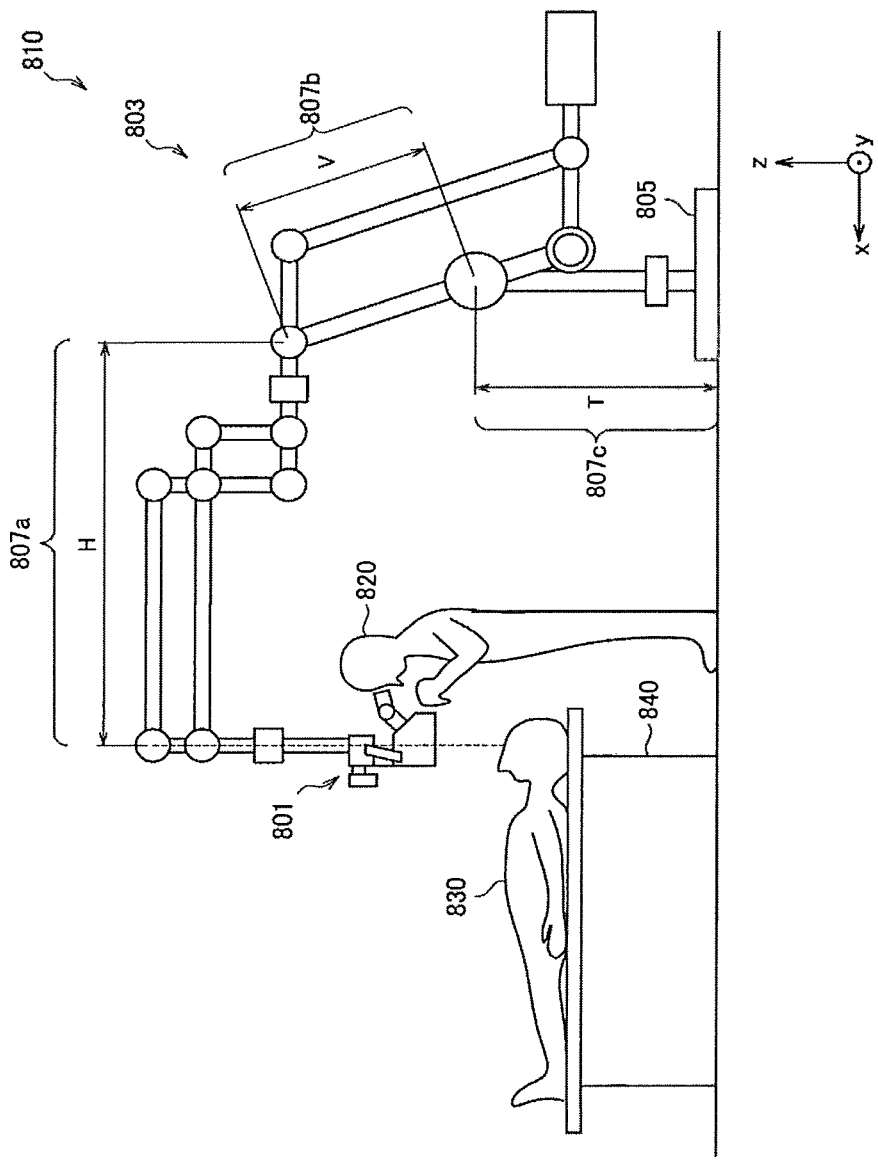
FIG. 1 is a diagram illustrating an operation using an existing optical microscope device.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description will be now made in the following order.
1. Background Where the Present Disclosure Has Been Conceived
1-1. Consideration of Existing Optical Microscope Device
1-2. Study of Electronic Imaging Microscope Device
2. Design Idea of Support Unit of Microscope Device according to the Present Embodiment
2-1. Conditions Requested by Use Modes
2-2. Conditions Requested by Movable Range and Miniaturization
2-3. Condition Requested by Installation Position
2-4. Summary of Conditions
2-5. Specific Design Example of Support Unit
3. Configuration Example of Microscope Device
4. Use Examples of Microscope Device
4-1. Use Example in Operations at Standing Position
4-2. Use Example in Operations at Seated Position
5. Modifications
5-1. Modification in Which Rotary Shaft Is Added to Support Unit
5-2. Modification in Which Electrical Unit Is Added to Base Unit
5-3. Modification in Which Prop Unit Is Configured to Have Greater Length (T)
5-3-1. Overview of Microscope Device
5-3-2. Schematic Configuration of Microscope Device
5-3-3. Design Idea of Support Unit
5-3-4. Specific Design Example of Support Unit
5-3-5. Use Example of Microscope Device
5-4. Modification in Which Image Vibration Reduction Mechanism Is Included
6. Supplemental Information Here, a microscope device chiefly includes a microscope unit, a support unit that supports the microscope unit at the distal end, and a base unit that supports the proximal end of the support unit. The directions will be defined as follows to describe the configuration of the microscope device. That is, the following description defines the direction vertical to the floor on which the microscope device is installed as a z-axis direction. The z-axis direction will also be referred to as up-down direction or vertical direction. Further, the direction which is orthogonal to the z-axis direction, and in which the support unit extends as viewed from the base unit (direction in which the microscope unit is positioned as viewed from the base unit) is defined as an x-axis direction. The x-axis direction will also be referred to as front-back direction. Moreover, the direction that is orthogonal to both x-axis direction and z-axis direction is defined as a y-axis direction. The y-axis direction can be said to be the direction that is orthogonal to both vertical direction and front-back direction. Additionally, the direction parallel to the x-y plane will also be referred to as horizontal direction.

Further, when the configuration of the support unit of the microscope device is described, the following description also refers to the side on which the microscope unit is provided as distal-end side, distal-end part or the like, and refers to the side closer to the base unit as proximal-end side, proximal-end part, or the like.

Further, to describe the configuration of the support unit, the following description assumes for the sake of convenience that the support unit is divided into the three parts of a first arm, a second arm, and a prop unit (also see FIGS. 1 and 9, and the like described below).

The first arm is positioned the closest to the distal-end side among them. The microscope unit is provided onto the distal-end side of the first arm. The proximal end of the first arm is supported by the distal end of the second arm rotatably around a first rotation axis parallel to the y axis (i.e., orthogonal to both vertical direction and front-back direction). Specifically, the first arm is positioned between an optical axis of the microscope unit and the first rotation axis when the microscope unit is disposed such that the optical axis is substantially vertical.

The prop unit is positioned the closest to the proximal-end side of the support unit. The prop unit extends from the floor substantially in the vertical direction, and supports the proximal end of the second arm at the distal end rotatably around a second rotation axis parallel to the y axis (i.e., orthogonal to the vertical direction and the front-back direction).

The second arm is positioned between the first arm and the prop unit. The second arm can also be said to be positioned between the first rotation axis and the second rotation axis.

The second rotation axis between the prop unit and the second arm, and the first rotation axis between the second arm and the first arm are both orthogonal to the y-axis direction, namely both vertical direction and front-back direction.

Accordingly, if the rotation angle of the second arm with the prop unit around the second rotation axis, and the rotation angle of the first arm with the second arm around the first rotation axis are controlled, the position of the microscope unit in the vertical plane (in the x-z plane) is decided. Further, the length (H) of the first arm (i.e., distance (H) between the optical axis of the microscope unit and the first rotation axis when the microscope unit is disposed such that the optical axis is substantially vertical), the length (V) of the second arm (i.e., the movable range of the microscope unit in the vertical plane is decided on the basis of the distance (V) between the first rotation axis and the second rotation axis, and the length (T) of the prop unit.

In this way, the length (H) of the first arm, the length (V) of the second arm, and the length (T) of the prop unit are important parameters indicating the structure of the support unit and the movable range of the microscope unit. The following thus assumes that the support unit includes the first arm, the second arm, and the prop unit. The configuration of the support unit will be described, focusing, in particular, on the lengths of these three parts. Additionally, the following description uses the wording "length (T) of the prop unit" for the sake of convenience, but the length (T) actually means the length from the floor to the second rotation axis, namely the length of the prop unit including up to the base unit.

Further, the following describes, as a surgeon, a user who performs a variety of operations on a microscope device according to an embodiment of the present disclosure for the sake of convenience. The description does not, however, limit users who use the microscope device. A variety of operations on the microscope device may be executed by any user such as another medical staff member.

1. Background Where the Present Disclosure has Been Conceived

Before a preferred embodiment of the present disclosure is described, the background where the present inventors have conceived of the present disclosure will be described to clarify an object and advantageous effect of the present disclosure.

1-1. Consideration of Existing Optical Microscope Device

Considerations of the present inventors about an existing optical microscope device will be described with reference to FIG. 1. FIG. 1 is a diagram illustrating an operation using an existing optical microscope device. FIG. 1 illustrates that a surgeon 820 uses a microscope device 810 to operate on a patient 830 lying down on an operating table 840.

The microscope device 810 is an optical microscope device, and includes an optical microscope unit 801 for the magnified observation of an operative site (head in the illustrated example) of a patient, a support unit 803 that supports the microscope unit 801 at the distal end, and a base unit 805 that supports the proximal end of the support unit 803. Further, the support unit 803 is configured as a balance arm including a counterweight.

The microscope unit 801 of the microscope device 810 is pointed to an operative site of the patient 830 in an operation. The surgeon 820 looks through the ocular unit of the microscope unit 801, and performs an operation while directly observing an image of the operative site which is magnified by the microscope unit 801 at an appropriate magnification.

Here, the optical microscope unit 801 includes a component such as an ocular unit, and is larger and weighs more than an electronic imaging microscope unit described below. The support unit 803 is thus larger and weighs more to support the microscope unit 801. The weight of the counterweight is designed to allow the support unit 803 to balance as a whole. In a case where the support unit 803 is larger, the counterweight is also larger for balance. As a result, the entire device is larger.

If a large device is disposed near the operating table 840, the large device interferes with a surgeon or another medical staff member working. The microscope device 810 is favorably disposed such that the position of the base unit 805 is farther from the operating table 840. The support unit 803 can be configured to extend over the surgeon 820 to the area near the operating table 840 from the farther position. That is, as illustrated, the surgeon 820 comes under the support unit 803 of the microscope device 810 to observe an operative site in most cases, which is namely referred to as overhead style.

Designed on the assumption of use in the overhead style, the support unit 803 has a first arm 807a configured to be relatively long to allow the surgeon 820 to come under the support unit 803. As the first arm 807a is longer, the first arm 807a weighs all the more. Accordingly, the counterweight is further larger, and the entire device is also further larger.

In this way, the configuration of the support unit 803 of the optical microscope device 810 has to be larger to support the optical microscope unit 801 and enable use in the overhead style. As a result, the counterweight is also larger. Therefore, the configuration of the entire device also tends to be larger.

Meanwhile, the movable range of the microscope unit 801 (range within which the microscope unit 801 can arrive) is dependent on the length of the first arm 807a, the length of a second arm 807b, and the length of a prop unit 807c. If the second arm 807b is lengthened to secure the movable range, the configuration of the support unit 803 is still larger. Accordingly, the counterweight is extremely larger. To both secure the movable range of the microscope unit 801 and miniaturize the counterweight, the second arm 807b of the microscope device 810 is thus configured to be relatively short. To secure the movable range in the height direction (z-axis direction), the prop unit 807c is configured to be relatively long.

In summary, in a case where the length of the first arm 807a is represented as H, the length of the second arm 807b is represented as V, and the length of the prop unit 807c is represented as T, the support unit 803 of the existing optical microscope device 810 is configured such that "H>V and T>V" or "H>T>V" is satisfied at the request of the configuration, use mode, or the like of the microscope unit 801.

Considerations of the present inventors about the existing optical microscope device 810 have been described above with reference to FIG. 1.

1-2. Study of Electronic Imaging Microscope Device

Small and high-resolution image sensors have been easily available in recent years. Microscope devices are developed that include not the above-described optical microscope unit 801, but an electronic imaging microscope unit which can electronically image an operative site with an image sensor.

A surgeon looks through the ocular unit provided to the optical microscope unit 801 to observe an operative site, and the attitude of the observing surgeon is limited by the position of the ocular unit (i.e., attitude of the microscope unit 801). In a case where the surgeon wants to observe an operative site at every angle, the surgeon also has to change his or her attitude in accordance with a change in the attitude of the microscope unit 801, which is not convenient. Further, it is not possible to observe an operative site from a direction in which the ocular unit is located at a position where a surgeon cannot look through. Accordingly, the range in which the surgeon can observe is substantially limited. The movable range required of the microscope unit is also limited.

Meanwhile, the electronic imaging microscope device including an electronic imaging microscope unit displays an image of an operative site captured by the microscope unit on a display device installed in an operating room, and a surgeon performs an operation while observing the image of the operative site shown on the display device. There is thus no restriction on the relative positional relationship between the surgeon and the microscope unit. It is possible to observe an operative site from every angle, and the surgeon can observe the operative site in a more comfortable attitude. In this way, the electronic imaging microscope device can further improve the convenience of the surgeon.

Here, it is possible that the structure of the support unit appropriate for the electronic imaging microscope device is not necessarily the same as that of the support unit 803 of the above-described optical microscope device 810.

For example, it is not necessary to provide a component such as an ocular unit to the electronic imaging microscope unit, and it is therefore possible to make the electronic imaging microscope unit much smaller than the optical microscope unit 801. It is thus possible to further miniaturize the configuration of the support unit that supports the microscope unit and the counterweight in the electronic imaging microscope device, and there is the probability that the configuration of the entire device is also miniaturized. The miniaturized device does not interfere with a surgeon or another medical staff member working even if the base unit is installed at a position closer to an operating table. A mode is thus assumed in which the electronic imaging microscope device is installed closer to an operating table and used. Use in the overhead style is not necessarily premised.

Further, as described above, the movable range required of the microscope unit 801 of the optical microscope device 810 is substantially limited to a partial area because of the positional relationship between the ocular unit and a surgeon. It is, however, possible to observe an operative site from any angle in the electronic imaging microscope device, and a wider movable range is therefore required of the microscope unit thereof.

Moreover, with respect to the electronic imaging microscope device, a surgeon performs an operation while watching the display device. The electronic imaging microscope device requires the support unit and the microscope unit to be disposed such that the view of the surgeon observing the display device is obstructed as little as possible. If the configuration compatible with the overhead style is applied to the electronic imaging microscope device, the distal-end part of the support unit and the microscope unit are hung over a surgeon and positioned in front of the eyes of the surgeon. Accordingly, the support unit and the microscope unit probably obstruct the view of the surgeon even if the microscope unit is small. It would not be thus the optimum use method to use the electronic imaging microscope device in the overhead style, in which the microscope unit is positioned in front of the eyes of a surgeon.

In this way, the configuration of the microscope unit, the movable range required of the microscope unit, the use mode, or the like of an electronic imaging microscope device are different from those of an optical microscope device. Accordingly, in a case where the configuration of the support unit in the optical microscope device as described with reference to FIG. 1 is directly applied to the electronic imaging microscope device, the configuration is not always appropriate for the electronic imaging microscope device. On the contrary, the configuration can decrease the convenience of a surgeon.

In view of the above-described circumstances, the support unit of the electronic imaging microscope device is required to be configured in consideration of the characteristics, use mode, or the like of the electronic imaging microscope device to further improve the convenience of a surgeon. The present inventors then have actively studied a configuration that is more appropriate for the electronic imaging microscope device and can further improve the convenience of a surgeon, and consequently conceived of the present disclosure. The following describes, in detail, a preferred embodiment of the present disclosure of which the present inventors have conceived.

2. Design Idea of Support Unit of Microscope Device according to the Present Embodiment Before the specific configuration of a microscope device according to a preferred embodiment of the present disclosure is described, the design idea of the support unit of the microscope device according to the present embodiment will be described with reference to FIGS. 2 to 8. A specific configuration example of the microscope device according to the present embodiment will be described again in (3. Configuration Example of Microscope Device) below. Additionally, FIGS. 2 to 8 below simplify the support unit for the sake of simplicity when illustrating the support unit of the microscope device, and schematically illustrate only the first arm, the second arm, and the prop unit thereof.

2-1. Conditions Requested by Use Modes

Figure 2:
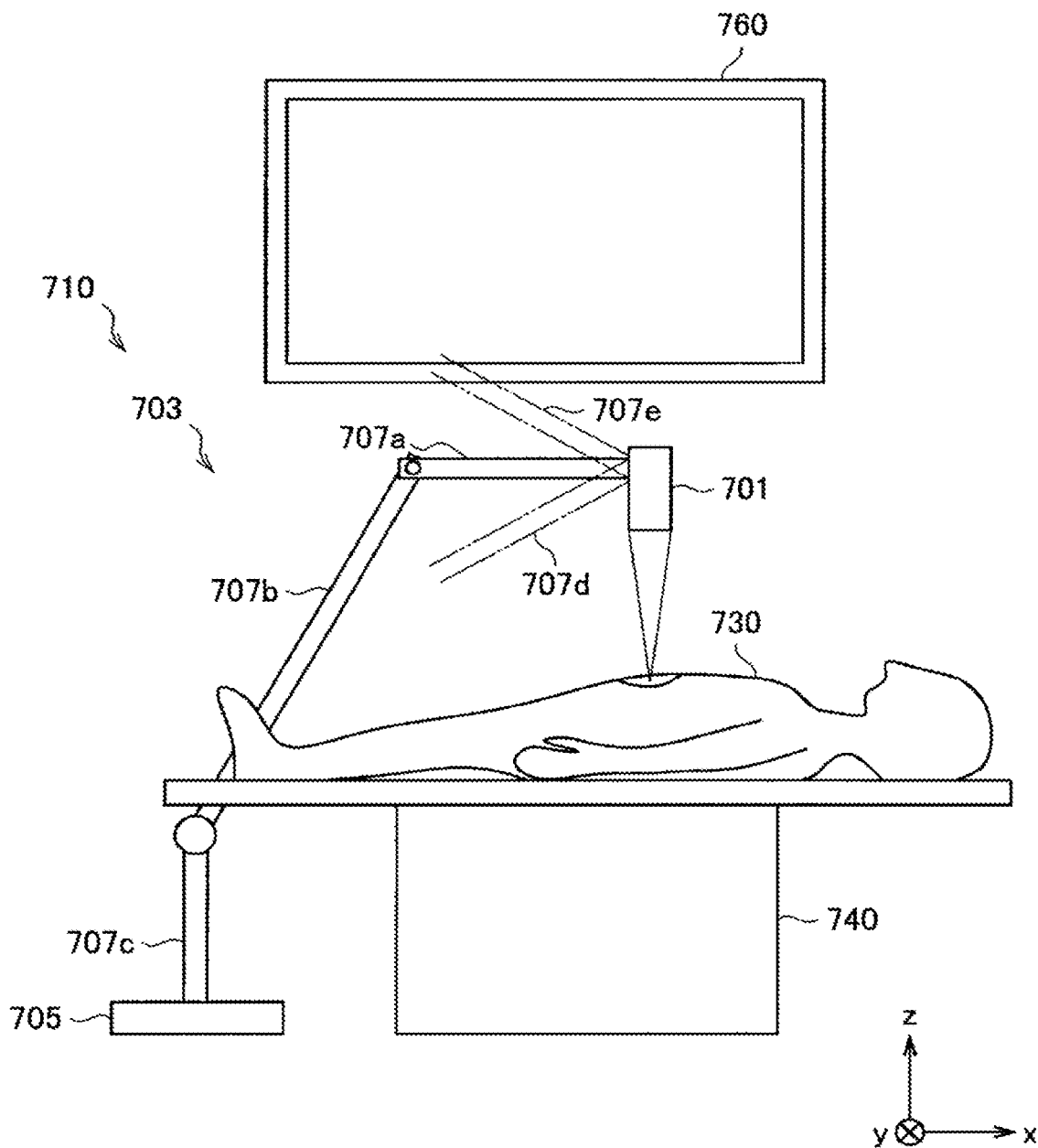
FIG. 2 is a diagram illustrating an operation using an electronic imaging microscope device.

FIG. 2 is a diagram illustrating an operation using an electronic imaging microscope device. FIG. 2 illustrates that a surgeon (not illustrated) uses a microscope device 710 to operate on a patient 730 lying down on an operating table 740.

The microscope device 710 is an electronic imaging microscope device, and includes an electronic imaging microscope unit 701 for the magnified observation of an operative site (stomach in the illustrated example) of a patient, a support unit 803 that supports the electronic imaging microscope unit 701 at the distal end, and a base unit 705 that supports the proximal end of the support unit 703. Additionally, FIG. 2 does not illustrate, but the support unit 703 includes a counterweight and is configured as a balance arm.

FIG. 2 also illustrates a display device 760 that displays an image of an operative site captured by the microscope unit 701. The surgeon performs an operation while watching the image of the operative site displayed on the display device 760. Additionally, the present embodiment assumes that the display device 760 is installed such that the display device 760 can be positioned substantially right in front of the surgeon when an operation is performed at the standing position.

In consideration of such a use mode, it is preferable to position the microscope unit 701 below the display device 760 (closer side to the operative site) as illustrated to secure the view of the surgeon watching the display device 760. Meanwhile, the space between the microscope unit 701 and the operative site is required to be wide to some extent to secure a working space that allows the surgeon to apply a variety of treatments to the operative site.

Here, for example, in a case where a first arm 707a extends downward from the microscope unit 701 (attitude like the attitude of a first arm 707d illustrated by the broken line in the figure) while the microscope unit 701 is positioned below the display device 760 to secure the view, the first arm 707a limits the working space.

Further, for example, in a case where a first arm 707a extends upward from the microscope unit 701 (like the attitude of a first arm 707e illustrated by the broken line in the figure) while the microscope unit 701 is positioned below the display device 760 to secure the view, the first arm 707a obstructs the view of a surgeon watching the display device 760.

To concurrently secure the view of the surgeon and the working space of the surgeon, it is thus preferable to configure the support unit 703 as illustrated such that the first arm 707a is substantially level when the microscope unit 701 images the operative site.

Figure 3:
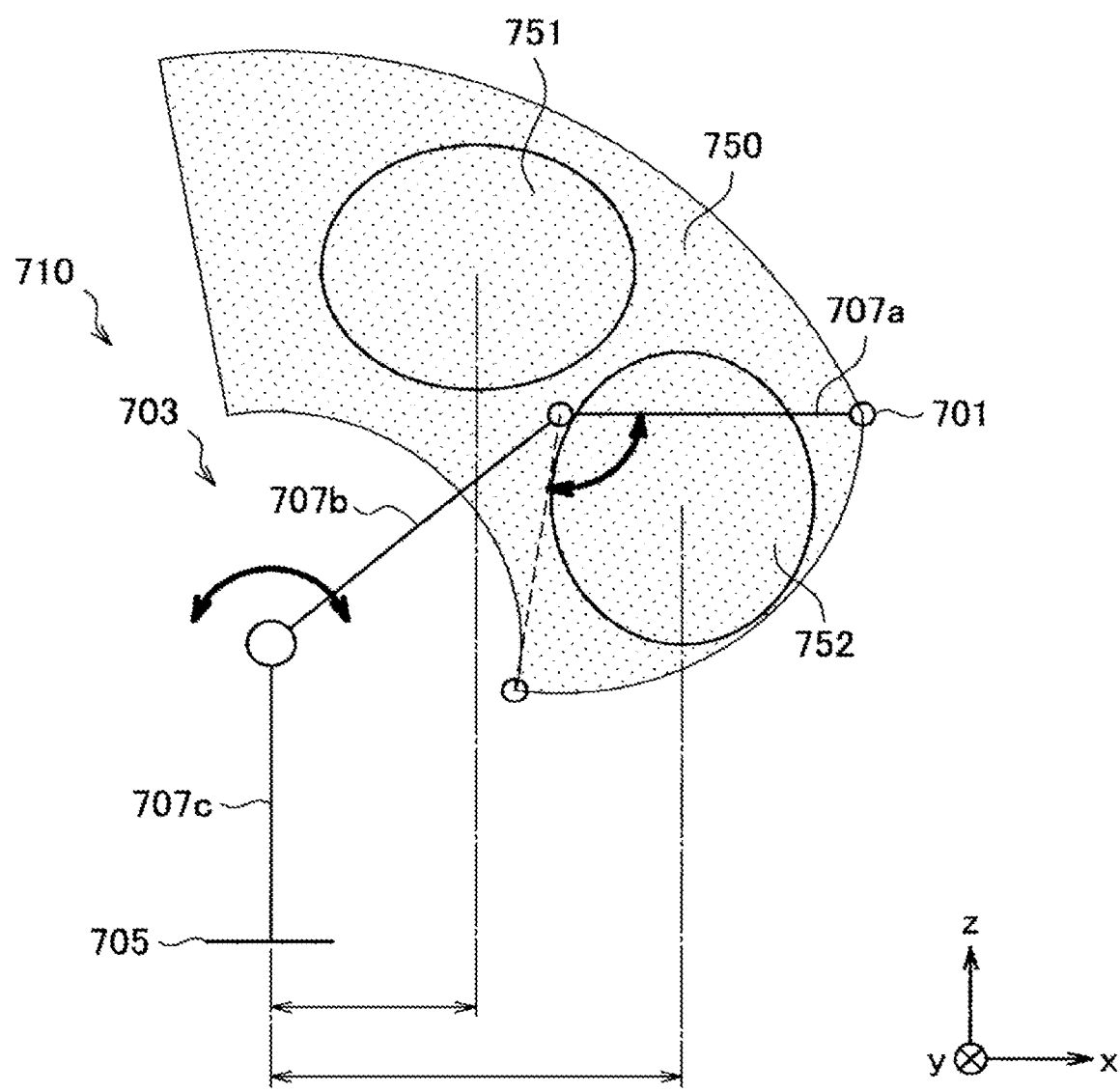
FIG. 3 is a schematic diagram illustrating a movable range of a microscope unit.

Here, the movable range of the microscope unit 701 will be considered with reference to FIG. 3. FIG. 3 is a schematic diagram illustrating the movable range of the microscope unit. FIG. 3 hatches a movable range 750 of the microscope unit 701. The microscope unit 701 is not, however, illustrated in detail, but simply represented as a circle.

As illustrated in FIG. 3, the movable range 750 of the microscope unit 701 can be an area enclosed by two arcs having different radii. The radii of these arcs, namely the size of the movable range 750 of the microscope unit 701, is dependent on the length (H) of the first arm 707a and the length (V) of a second arm 707b.

Here, the movable range of the microscope unit 701 in the vertical direction will be considered. In a case where the first arm 707a is kept substantially level, the length (H) of the first arm 707a does not contribute to the movable range of the microscope unit 701 in the vertical direction. The movable range is dependent on the length (V) of the second arm 707b. For example, in a case where the support unit 703 is configured like the above-described optical microscope device 810 such that the length (H) of the first arm 707a is greater than the length (V) of the second arm 707b (i.e., in a case where V is relatively short), the movable range of the microscope unit 701 in the vertical direction is thus considerably limited. If the support unit 703 configured such that the length (H) of the first arm 707a is greater than the length (V) of the second arm 707b considerably moves the microscope unit 701 in the vertical direction, it is no longer possible to keep the first arm 707a level. It is possible that the first arm 707a obstructs the view of a surgeon or interferes with the working space of a surgeon like the first arms 707d and 707e illustrated in FIG. 2.

Meanwhile, operations include operations performed by a surgeon in a standing attitude (standing position) and operations performed by a surgeon in a seated attitude (seated position). The microscope unit 701 is positioned right above the operating table 740 in an operation. The height of the operating table 740 is, however, different between the standing position and the seated position, and the use area (area in which the microscope unit 701 can be positioned in imaging an operative site) of the microscope unit 701 is also different in height. If the movable range of the microscope unit 701 in the vertical direction is narrow, it is thus difficult to cover both operations at the standing position and operations at the seated position.

To cover both operations at the standing position and operations at the seated position (i.e., to secure the microscope unit 701 a wider movable range in the vertical direction) while keeping the first arm 707a substantially level, it is thus preferable to configure the support unit 703 such that the length (V) of the second arm 707b is greater than the length (H) of the first arm 707a. That is, one of the conditions (which will also be referred to as "conditions requested by the use modes" for the sake of convenience) required of the support unit 703 to cover both operations at the standing position and operations at the seated position while keeping the first arm 707a substantially level is expressed like (Condition 1) below.

$$V > H \quad \text{(Condition 1)}$$

Additionally, although the details will be described again in (4. Use Examples of Microscope Device) below, the distance between the prop unit 707c and the operating table 740 is adjusted in the present embodiment in a case where both operations at the standing position and operations at the seated position are covered while the first arm 707a is kept substantially level.

Specifically, as illustrated in FIG. 3, the movable range 750 of the microscope unit 701 respectively grows higher and lower as the movable range 750 of the microscope unit 701 comes closer to and gets farther away from the prop unit 707c. In a case where an operation is performed at the standing position, the microscope device 710 can thus be installed to position the prop unit 707c closer to the operating table 740 such that a use area 751 (use area 751 at the standing position) of the microscope unit 701 in an operation at the standing position, at which the use area 751 is disposed at a higher position, is included in the movable range 750. If the attitude of the support unit 703 is adjusted to incline the second arm 707b at the substantially perpendicular angle with the prop unit 707c brought closer to the operating table 740, it is possible to dispose the microscope unit 701 at a higher position right above the operating table 740 while keeping the first arm 707a substantially level. Accordingly, it is possible to dispose the microscope unit 701 in the use area 751 at the standing position.

Meanwhile, in a case where an operation is performed at the seated position, the microscope device 710 can thus be installed to position the prop unit 707c relatively far from the operating table 740 such that a use area 752 (use area 752 at the seated position) of the microscope unit 701 in an operation at the seated position, at which the use area 751 is disposed at a lower position, is included in the movable range 750. If the attitude of the support unit 703 is adjusted to incline the second arm 707b toward the operating table 740 with the prop unit 707c brought relatively far from the operating table 740, it is possible to dispose the microscope unit 701 at a lower position right above the operating table 740 while keeping the first arm 707a substantially level. Accordingly, it is possible to dispose the microscope unit 701 in the use area 752 at the seated position.

Figure 4:
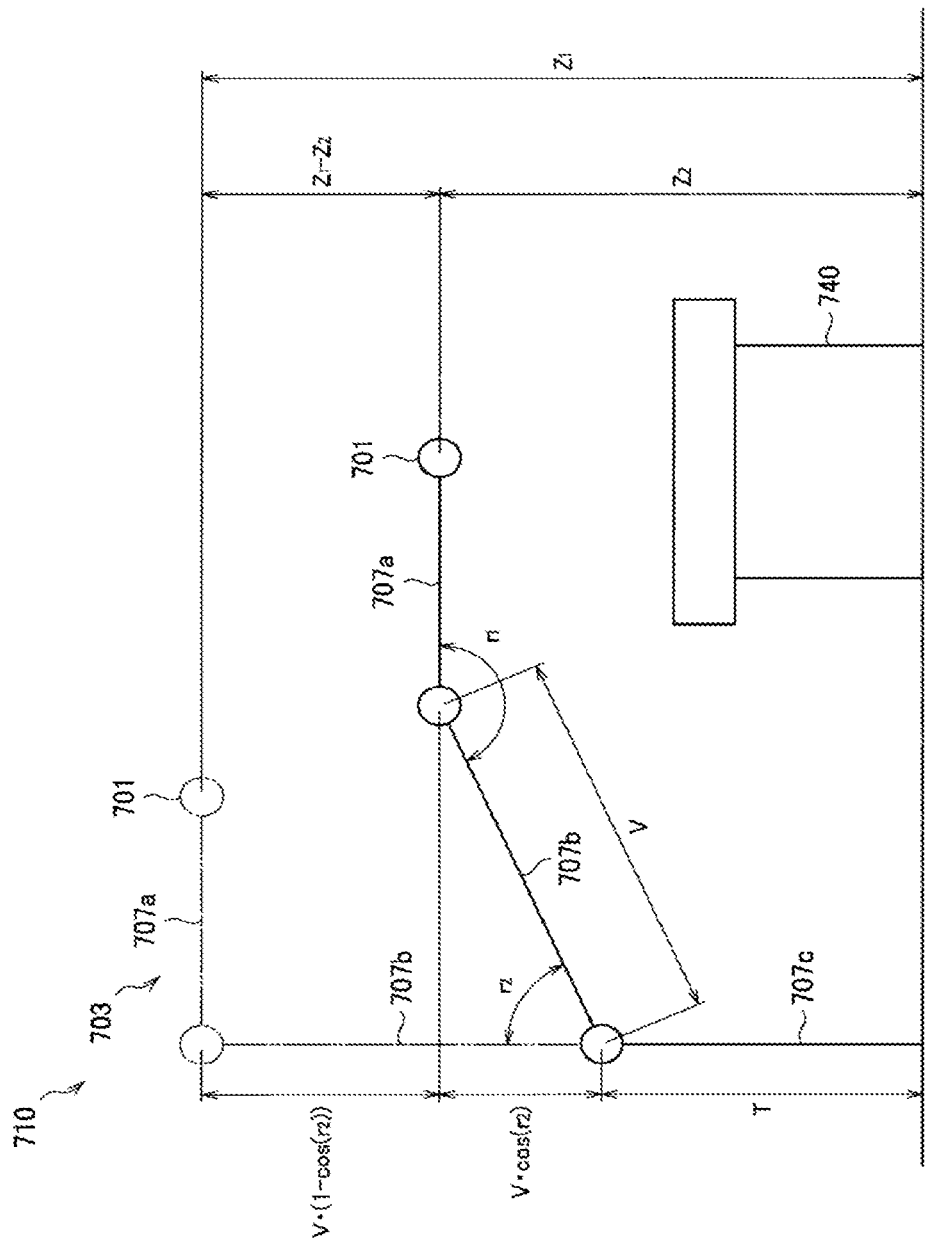
FIG. 4 is an explanatory diagram for describing a condition requested by a use mode.
Figure 5:
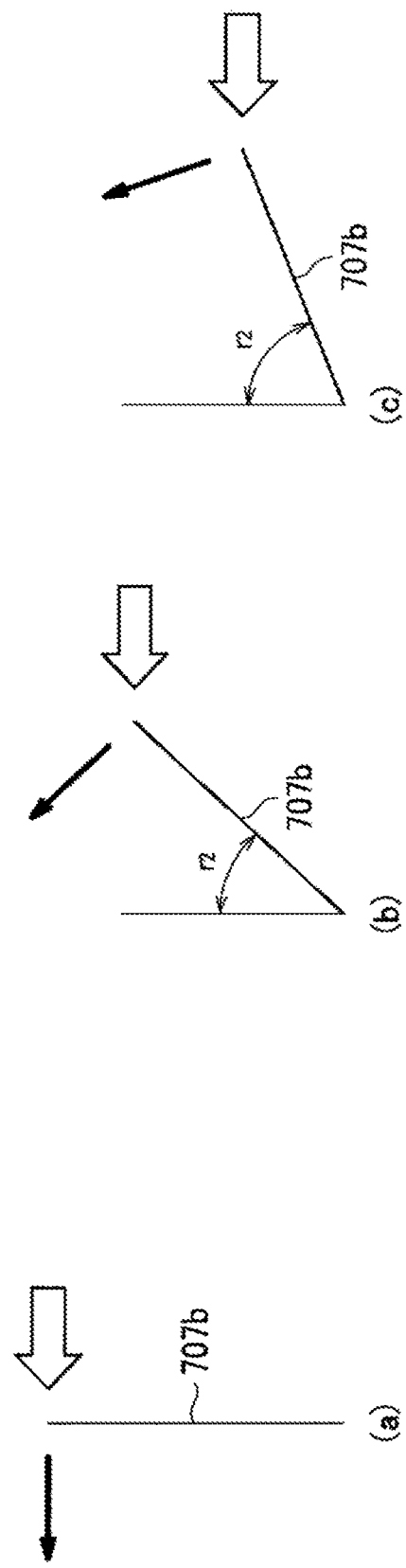
FIG. 5 is an explanatory diagram for describing a range of a maximum value $r_{2max}$ of a rotation angle $r_2$ of a second arm with a prop unit illustrated in FIG. 4.

Here, the conditions requested by the use modes will be described in more detail with reference to FIGS. 4 and 5. FIG. 4 is an explanatory diagram for describing the conditions requested by the use modes. FIG. 4 schematically illustrates the positional relationship between the support unit 703 of the microscope device 710 and the operating table 740. Additionally, FIG. 4 simplifies the microscope unit 701 similarly to FIG. 3 for the sake of simplicity. Further, FIG. 5 is an explanatory diagram for describing the range of a maximum value $r_{2max}$ of a rotation angle $r_2$ (rotation angle $r_2$ of the second rotation axis) of the second arm 707b with the prop unit 707c illustrated in FIG. 4.

The height (which will also be referred to as standing position height) of an objective lens provided near the lower end of the microscope unit 701 in an operation at the standing position is represented as $Z_1$, and the height (which will also be referred to as seated position height) of the objective lens of the microscope unit 701 in an operation at the seated position is represented as $Z_2$. To satisfy the conditions requested by the use modes, the support unit 703 only has to be configured as illustrated in FIG. 4 such that the objective lens of the microscope unit 701 can be positioned at the standing position height $Z_1$ with the second arm 707b extending substantially in the vertical direction, and the objective lens of the microscope unit 701 can be positioned at the seated position height $Z_2$ with the second arm 707b inclined (rotated) to the prop unit 707c at the predetermined angle $r_2$. In other words, the support unit 703 only has to be configured such that, in a case where the second arm 707b extending substantially in the vertical direction is changed to be rotated from the prop unit 707c at the predetermined angle $r_2$, the objective lens of the microscope unit 701 can be changed in the height direction by the amount of change $(Z_1-Z_2)$ between the standing position height $Z_1$ and the seated position height $Z_2$.

That is, the support unit 703 can be configured such that (Condition 2) and (Condition 3) below are satisfied.

$$Z_1 - Z_2 < V(1 - \cos(r_2)) \quad \text{(Condition 2)}$$

$$Z_2 > V \cos(r_2) + T \quad \text{(Condition 3)}$$

Here, if a surgeon of average stature is assumed, the amount of change $Z_1-Z_2$ between the standing position height $Z_1$ and the seated position height $Z_2$ equals at least approximately 200 (mm). Taking it into consideration that surgeons of any stature can be covered, approximately 200 (mm)<$Z_1-Z_2$<approximately 400 (mm) is preferable as the range of $Z_1-Z_2$ to cover both a case where a surgeon who is, for example, 2 m tall performs an operation at the standing position, and a surgeon who is 1.5 m tall performs an operation at the seated position.

Further, the microscope unit 701 can be more considerably changed in the height direction with an increase in the rotation angle $r_2$ of the second arm 707b with the prop unit 707c. It is, however, necessary to set an upper limit for the rotation angle $r_2$ from the perspective of operability. FIG. 5 schematically illustrates the second arm 707b. The force applied to the distal end of the second arm 707b when the microscope unit 701 is moved is represented as a thick arrow. The direction in which the second arm 707b is rotated by the force is represented as a thin arrow. In a case where the rotation angle $r_2$ is substantially 0° as illustrated in FIG. 5(a), the force application direction substantially agrees with the rotation direction of the second arm 707b. Accordingly, the second arm 707b is rotated by relatively small force, and it is consequently possible for a surgeon to move the microscope unit 701 with relatively small force.

As illustrated in FIGS. 5(b) and (c), the force application direction, however, disagrees with the rotation direction of the second arm 707b as the rotation angle $r_2$ increases. In a case where the rotation angle $r_2$ is large, it is thus difficult to rotate the second arm 707b and a surgeon needs relatively great force to move the microscope unit 701. That is, in a case where the rotation angle $r_2$ is excessively large, the operability of a surgeon to move the microscope unit 701 can be decreased. If the maximum value of the rotation angle $r_2$ is represented as $r_{2max}$, it is thus preferable to set a range of approximately 45°<$r_{2max}$<approximately 60° for $r_{2max}$ not to decrease the operability of the surgeon more than necessary, but to secure the amount of change in the microscope unit 701 in the height direction.

In a case where the length (V) of the second arm 707b is actually designed, a specific length V may be designed in consideration of the above-described range that $Z_1$-$Z_2$ can have and the above-described range that $r_{2max}$ can have. As an example, if $Z_1$-$Z_2$=200 (mm) and $r_{2max}$=45° are substituted into the above-described expression (2), approximately 683 (mm)<V is obtained.

Additionally, it is preferable from the perspective of device miniaturization to design the length (V) of the second arm 707b as $Z_1$-$Z_2$=200 (mm) and $r_{2max}$=60°. In this case, approximately 400 (mm)<V is obtained, and the length (V) of the second arm 707b can be the shortest. Accordingly, it is possible to further miniaturize the device.

The conditions requested by the use modes have been described above. In summary, it is preferable because of the conditions requested by the use modes to configure the support unit 703 such that the conditions expressed as (Condition 1) to (Condition 3) above are satisfied.

2-2. Conditions Requested by Movable Range and Miniaturization

The support unit 703 of the microscope device 710 is required to be configured such that the movable range of the microscope unit 701 satisfies a desired range. Here, the movable range of the microscope unit 701 is dependent on the length (H) of the first arm 707a, the length (V) of the second arm 707b, the length (T) of the prop unit 707c, the rotation angle $r_1$ (rotation angle $r_1$ of the first rotation axis) of the first arm 707a from the second arm 707b, and the rotation angle $r_2$ (rotation angle $r_2$ of the second rotation axis) of the second arm 707b with the prop unit 707c. Accordingly, if these values are increased, it is possible to increase the movable range of the microscope unit 701. However, if these values are increased more than necessary, the support unit 703 is larger and the configuration of the entire device is also larger. As described above, the microscope device 710 has the advantage that the electronic imaging microscope unit 701 can be configured to be smaller and weigh less than the optical microscope unit 801, and the configuration of the entire microscope device 710 can be therefore still smaller. Accordingly, to make use of this advantage, it is not preferable that the device be larger even if a wider movable range can be obtained.

That is, it is preferable to configure the support unit 703 of the microscope device 710 to remain small and allow the microscope unit 701 to have a desired movable range. The following describes, in more detail, the conditions (which will also be referred to as "conditions requested by the movable range and miniaturization" for the sake of convenience) required for the support unit 703 to remain small and allow the microscope unit 701 to have a desired movable range.

First, the movable range of the microscope unit 701 will be described. The movable range required of the microscope unit 701 is defined on the basis of the arrivable distance (which will be referred to as horizontal required arrival distance (WH)) from the prop unit 707c in the horizontal direction which is required of the objective lens of the microscope unit 701, and the arrivable distance (which will be referred to as vertical required arrival distance (WV)) from the floor in the vertical direction which is required of the objective lens of the microscope unit 701 in the present embodiment. If the objective lens of the microscope unit 701 can pass through the positions in the space corresponding to the horizontal required arrival distance (WH) and the vertical required arrival distance (WV), it can be said that the microscope unit 701 has a sufficient movable range. In other words, to allow the microscope unit 701 to have a sufficient movable range, it is preferable to configure the support unit 703 such that the objective lens of the microscope unit 701 passes through the positions in the space corresponding to the horizontal required arrival distance (WH) and the vertical required arrival distance (WV).

Figure 6:
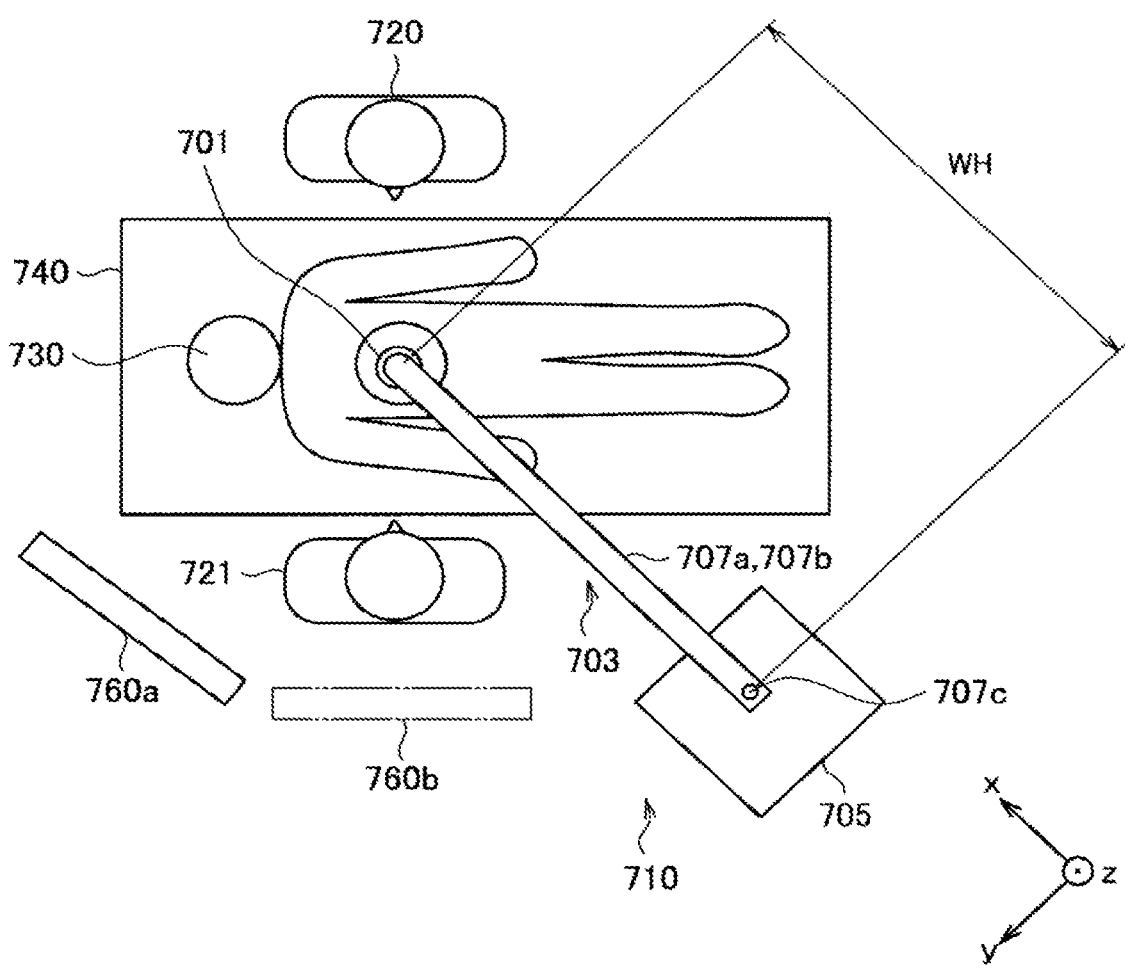
FIG. 6 is an explanatory diagram for describing a horizontal required arrival distance (WH) in the electronic imaging microscope device.
Figure 7:
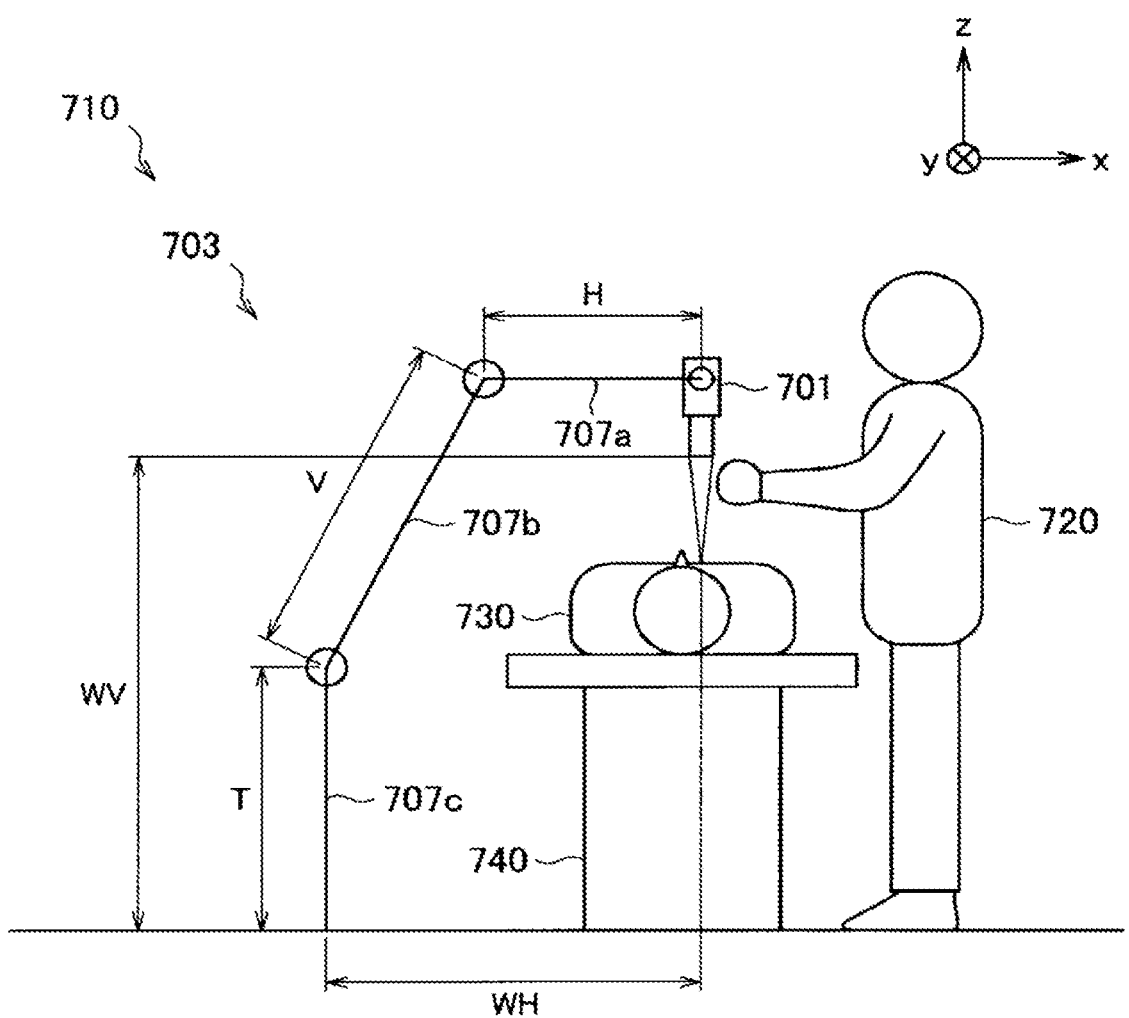
FIG. 7 is an explanatory diagram for describing a vertical required arrival distance (WV) in the electronic imaging microscope device.

The movable range of the microscope unit 701 will be described in more detail with reference to FIGS. 6 and 7. FIG. 6 is an explanatory diagram for describing the horizontal required arrival distance (WH) in the electronic imaging microscope device. FIG. 7 is an explanatory diagram for describing the vertical required arrival distance (WV) in the electronic imaging microscope device.

FIGS. 6 and 7 each illustrate that a surgeon 720 uses a microscope device 710 to operate on a patient 730 lying down on an operating table 740 similarly to FIG. 2. Additionally, FIG. 6 is a top view looking down on an operation, and FIG. 7 illustrates an operation from the horizontal direction. Further, FIG. 6 illustrates not only the surgeon 720 who performs an operation, but also an assistant 721 who assists in the operation.

The horizontal required arrival distance (WH) is decided, on the basis of the positional relationship between the microscope device 710 and the operating table 740, or more specifically the distance between the prop unit 707c and the operating table 740, such that the objective lens of the microscope unit 701 can be positioned substantially right above an operative site.

Specifically, a position at which the microscope device 710 can be actually installed is decided by assuming the position of the surgeon 720, the position of the assistant 721, the position of the display device 760, and the position of the patient 730 (position of an operative site) in an actual operation as illustrated in FIG. 6. The horizontal required arrival distance (WH) is then decided such that the objective lens of the microscope unit 701 can arrive substantially right above the operative site from the installation position. To make the configuration of the support unit 703 as small as possible, it is preferable at this time to install the prop unit 707c as close to the operating table 740 as possible and decide as short the distance WH as possible.

The above-described positions of the surgeon 720 and the like can be, however, changed in accordance with the operation modes. For example, in a case where the assistant 721 is positioned to face the surgeon 720, a display device 760a can be disposed in the oblique direction from the surgeon as illustrated. Meanwhile, in a case where the assistant 721 is not positioned to face the surgeon 720, it is also possible that a display device 760b is disposed to face the surgeon (illustrated by the two-dot chain line). It is thus preferable to decide the distance WH by changing the positions of the surgeon 720 and the like as appropriate in accordance with the possible operation modes to cover the various operation modes.

A result of consideration of the present inventors who assumes a general operation mode on the condition that the prop unit 707c is installed as close to the operating table 740 as possible reveals that it is possible to move the microscope unit 701 to a position at which any operation mode can be covered at least in the horizontal direction, for example, by configuring the support unit 703 such that the horizontal required arrival distance (WH)=approximately 800 (mm) is satisfied. The numerical value is, however, merely an example. The distance WH can be decided as appropriate in accordance with an operation mode that can be actually adopted.

The vertical required arrival distance (WV) is decided on the basis of the height (B) of the operating table 740, the body height of the patient 730 lying down on the operating table 740 in the vertical direction (which will be referred to simply as body height of the patient 730), and the working distance (WD) of the microscope unit 701 such that the objective lens of the microscope unit 701 can be disposed at a position at which an appropriate image can be captured on the substantially right above the operative site. Specifically, the value of the distance WV is decided such that the WV is substantially equal to the total value of the height (B) of the operating table 740, the body height of the patient 730, and the WD of the microscope unit 701.

As illustrated in FIG. 7, the patient 730 (operative site) and the operating table 740 are positioned on the optical axis of the microscope unit 701 in the vertical direction when an image is captured. If the distance WV is decided such that the distance WV is substantially equal to the total value of the height (B) of the operating table 740, the body height of the patient 730, and the WD of the microscope unit 701, the microscope unit 701 is thus disposed such that the microscope unit 701 can appropriately image the operative site. It is actually possible that the operative site is obliquely imaged. However, in a case where the microscope unit 701 is moved to image the operative site at different angles with the WD of the microscope unit 701 kept constant, the microscope unit 701 is moved on a hemisphere around the operative site. In a case where the operative site is imaged from above in the vertical direction as illustrated, the objective lens of the microscope unit 701 reaches the highest positon. Accordingly, if the support unit 703 is configured such that the WV in this case is satisfied, the other attitudes can also be achieved.

Here, the WD of the microscope unit 701 corresponds to the focal distance of the objective lens provided near the lower end of the microscope unit 701. Accordingly, in a case where the focal distance is variable, it is preferable to decide the distance WV in consideration of the maximum value and the minimum value of the focal distance (i.e., the maximum value and the minimum value of the WD).

A result of consideration of the present inventors who assume the typical size of the operating table 740, the typical body shape of the patient 730, and the typical optical property of the microscope unit 701 (e.g., the height (B) of the operating table 740=800 (mm) or the like) reveals that if the support unit 703 is configured, for example, such that the vertical required arrival distance (WV)=approximately 1600 (mm) is satisfied, it is possible to move the objective lens of the microscope unit 701 at a position at least in the vertical direction at which an appropriate image can be captured. The numerical value is, however, merely an example. The distance WV can be decided as appropriate in accordance with the size of the operating table 740, the optical property of the microscope unit 701, or the like which can be actually used.

In summary, in a case where a typical condition such as the size of the operating table 740 is assumed, it is preferable to configure the support unit 703 such that (Condition 4) below is satisfied, in order to achieve the sufficient movable range of the microscope unit 701 which can cover any use mode.

> The objective lens of the microscope unit 701 passes through a position in the space of
> $WH$=approximately 800 (mm) and
> $WV$=approximately 1600 (mm).  (Condition 4)

Additionally, as illustrated in FIG. 7, the vertical required arrival distance (WV) is decided on the assumption of operations at the standing position. As described above with reference to FIG. 3, operations at the standing position require the operating table 740 to have greater height (B) and the position of the use area of the microscope unit 701 to be higher than operations at the seated position do. That is, operations at the standing position require a wider movable range in the vertical direction (i.e., longer vertical required arrival distance (WV)) of the microscope unit 701 than operations at the seated position do. If the vertical required arrival distance (WV) is obtained on the assumption of operations at the standing position, it is thus possible to cover operations at the seated position, which require only a shorter vertical required arrival distance (WV). Specifically, as described above, the microscope device 710 is installed at a position farther from the operating table 740, and the attitude of the support unit 703 is adjusted to incline the second arm 707b more toward the operating table 740 in an operation at the seated position. This allows the microscope unit 701 to be disposed at a lower position.

Next, the miniaturization of the support unit 703 will be described. It is preferable to configure the support unit 703 to remain small and allow the microscope unit 701 to have the above-described movable range. Here, as described above, the movable range of the microscope unit 701 is dependent on the length (H) of the first arm 707a, the length (V) of the second arm 707b, the length (T) of the prop unit 707c, the rotation angle $r_1$ of the first arm 707a from the second arm 707b, and the rotation angle $r_2$ of the second arm 707b with the prop unit 707c. To achieve this, it is thus preferable to set upper limit values for the length (H) of the first arm 707a of the support unit 703, the length (V) of the second arm 707b, and the length (T) of the prop unit 707c, and set wider movable ranges for the rotation angle $r_1$ of the first arm 707a with the second arm 707b and the rotation angle $r_2$ of the second arm 707b with the prop unit 707c than the movable ranges thereof in the support unit of the existing optical microscope device.

For example, the upper limit value of the length of each part of the support unit 703 can be decided such that, in a case where the microscope device 710 is installed near the operating table 740, the microscope device 710 does not interfere with a surgeon and another medical staff member working. Further, the movable ranges of the rotation angle $r_1$ and the rotation angle $r_2$ are set such that the microscope unit 701 satisfies the movable range shown in (Condition 4) above in the support unit 703 configured to have the length of each part satisfy the decided upper limit value.

A result of consideration of the present inventors reveals that if the support unit 703 is configured such that (Condition 5) and (Condition 6) below are satisfied, it is possible to achieve the relatively small microscope device 710 while satisfying the movable range shown in (Condition 4) above.

$H+V+T$<approximately 2500 (mm)  (Condition 5)

approximately 130°<$r_1+r_2$<approximately 180° preferably, approximately 150°<$r_1+r_2$<approximately 180° more preferably, approximately 170°<$r_1+r_2$<approximately 180°  (Condition 6)

The conditions requested by the movable range and miniaturization have been described above. In summary, it is preferable because of the conditions requested by the movable range and miniaturization to configure the support unit 703 such that the conditions expressed as (Condition 4) to (Condition 6) above are satisfied.

Figure 8:
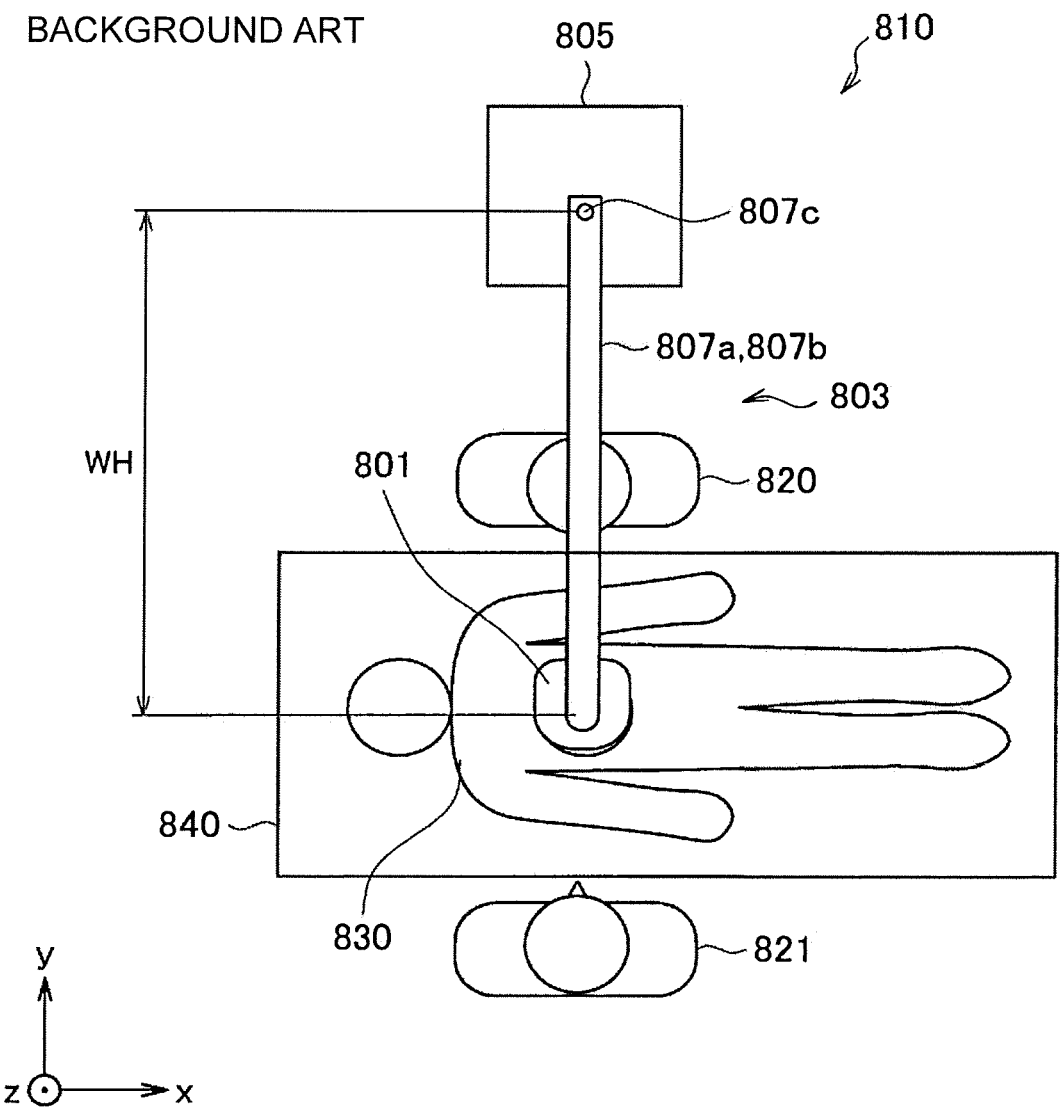
FIG. 8 is an explanatory diagram for describing the horizontal required arrival distance (WH) in the optical microscope device.

Here, the movable range (i.e., the horizontal required arrival distance (WH) and the vertical required arrival distance (WV)) required of the microscope unit 801 in the optical microscope device 810 illustrated in FIG. 1 will be described with reference to FIG. 8 for comparison. FIG. 8 is an explanatory diagram for describing the horizontal required arrival distance (WH) in the optical microscope device.

FIG. 8 illustrates that the surgeon 820 uses the optical microscope device 810 to operate on the patient 830 lying down on the operating table 840 similarly to FIG. 1. Additionally, FIG. 8 is a top view looking down on an operation. Further, FIG. 8 illustrates not only the surgeon 820 who performs an operation, but also an assistant 821 who assists in the operation.

As illustrated in FIG. 8, the optical microscope device 810 is installed at a position relatively far from the operating table 840. Accordingly, the horizontal required arrival distance (WH) is longer than the distance WH (800 (mm) in the above-described example) of the electronic imaging microscope device 710. Further, as described above with reference to FIG. 1, the surgeon 820 comes under the support unit 803 of the optical microscope device 810 to perform an operation. Accordingly, the vertical required arrival distance (WV) is also longer than the distance WV (1600 (mm) in the above-described example) of the electronic imaging microscope device 710.

In this way, the length required of the support unit 703 of the electronic imaging microscope device 710 to achieve a desired movable range is extremely shorter than that of the optical microscope device 810. If the support unit 703 is short, the support unit 703 weighs all the less and it is possible to miniaturize the counterweight. The electronic imaging microscope device 710 thus makes it possible to both miniaturize the device and secure a desired movable range.

Additionally, for reference, a model of the existing optical microscope device 810 which is said to have a relatively wide movable range for the support unit has a joint unit movable range of approximately 0° to 50° which corresponds to the rotation angle $r_2$, and a joint unit movable range of approximately −40° to +40° which corresponds to the rotation angle $r_1$. That is, expressed to correspond to (Condition 6) above, the movable range of the rotation angle of the existing optical microscope device 810 is $r_1+r_2$<approximately 130°. If the length of each part of the support unit 703 is relatively short and the movable ranges of the rotation angle $r_1$ and the rotation angle $r_2$ are set wider than those of the existing microscope device in this way in the present embodiment, it is possible to miniaturize the device while securing the microscope unit 701 as wide a movable range as or a wider movable range than that of the existing device.

2-3. Condition Requested by Installation Position

As described above, the electronic imaging microscope unit 701 can be configured to be smaller and weigh less than the optical microscope unit 801, and the configuration of the entire microscope device 710 can be therefore still smaller. It is thus possible to install the microscope device 710 closer to the operating table 740.

Here, generally speaking, surgery has the concepts of a clean area and an unclean area. It is necessary to dispose no unclean device near the clean area. The area on the operating table 740 is a clean area. Accordingly, in a case where the microscope device 710 is disposed close to the operating table 740, the microscope unit 701 and the support unit 703 of the microscope device 710 are covered with drapes shaped like bags.

However, if the entire microscope device 710 is covered with a drape, a large drape is necessary. Accordingly, only the parts corresponding to the first arm 707a and the second arm 707b are usually covered with drapes, and the part corresponding to the prop unit 707c is exposed in many cases. If the length (T) of the prop unit 707c is greater than the height (B) of the operating table 740, the prop unit 707c can thus invade the clean area.

Here, the top of the operating table 740 is a clean area, but the lower area than the operating table 740 is an unclean area. If the length (T) of the prop unit 707c is shorter than the height (B) of the operating table, there is thus no possibility that the prop unit 707c invades the clean area in spite of the microscope device 710 being installed close to the operating table 740. In other words, to install the microscope device 710 closer to the operating table 740, it is preferable to configure the support unit 703 such that (Condition 7) below is satisfied.

$$T<B \quad \text{(Condition 7)}$$

For example, the operating table 740 generally used has a height (B) of approximately 800 (mm). The support unit 703 can be thus configured favorably, for example, such that the length (T) of the prop unit 707c is 800 (mm) or shorter. The following also refers to the condition (B>T) required of the support unit 703 as "condition requested by the installation position" for the sake of convenience.

2-4. Summary of Conditions

The three conditions described above will be summarized.
(Conditions Requested by Use Modes)
Object:
To cover both operations at the standing position and operations at the seated position (secure the microscope unit 701 a wider movable range in the up-down direction) while keeping the first arm 707a substantially level.
Conditions Required of the Support Unit:

$$V>H \quad \text{(Condition 1)}$$

$$Z_1-Z_2<V(1-\cos(r_2)) \quad \text{(Condition 2)}$$

$$Z_2>V\cos(r_2)+T \quad \text{(Condition 3)}$$

(Conditions Requested by Movable Range and Miniaturization)
Object:
To further miniaturize the configuration of the support unit 703 while securing the microscope unit 701 a movable range that can cover a variety of operation modes.

The objective lens of the microscope unit 701 passes through a position in the space corresponding to the horizontal required arrival distance (WH) (e.g., WH=approximately 800 (mm)) and the vertical required arrival distance(WV)(e.g., WV=approximately 1600 (mm)), which are the arrival distances required to capture an appropriate image. (Condition 4)

$$H+V+T<\text{approximately 2500 (mm)} \quad \text{(Condition 5)}$$

approximately 130°<$r_1+r_2$<approximately 180° preferably, approximately 150°<$r_1+r_2$<approximately 180° more preferably, approximately $170°<r_1+r_2<$approximately $180°$ (Condition 6)

(Condition Requested by Installation Position)
Object:
To secure a clean area while installing the microscope device 710 closer to the operating table 740.
Conditions Required of the Support Unit:

$T<B$ (Condition 7)

The support unit 703 is configured in the present embodiment such that at least (Condition 1) above is satisfied. More specifically, the support unit 703 may be configured such that (Condition 2) above and (Condition 3) above are further satisfied. This can keep the first arm 707a substantially level in an operation, and secure the working space of a surgeon and the view of a surgeon. Accordingly, it is possible to further improve the convenience of the surgeon. At this time, it is possible to keep the first arm 707a substantially level in both operations at the standing position and operations at the seated position, which can secure the working space of the surgeon and the view of the surgeon regardless of the operation modes.

Further, to allow the microscope unit 701 to have a desired movable range that can cover a variety of surgical procedures while keeping the microscope device 710 smaller, the support unit 703 can be configured such that the above-described conditions requested by the movable range and miniaturization (i.e., (Condition 4) above to (Condition 6) above) are satisfied. This can miniaturize the microscope device 710 while securing the microscope unit 701 a sufficient movable range that can cover a variety of surgical procedures. Accordingly, the convenience of a surgeon can be further improved.

Further, in a case where it is desirable to dispose the microscope device 710 near the operating table 740, the support unit 703 can be configured such that the above-described condition requested by the installation position (i.e., (Condition 7) above) is satisfied. This makes it possible to install the microscope device 710 closer to the operating table 740 while securing the clean area. Accordingly, it is possible to further miniaturize the support unit 703, and further miniaturize the configuration of the entire device.

2-5. Specific Design Example of Support Unit

The present inventors have actually designed the configuration of the support unit 703 which can satisfy each of the above-described conditions. Here, a design result will be described as an example in a case where the support unit 120 is configured such that the conditions requested by the use modes, the conditions requested by the movable range and miniaturization, and the condition requested by the installation position are satisfied (i.e., (Condition 1) above to (Condition 7) above are satisfied).

Specifically, the upper limit value of the length (V) of the second arm 707b can be decided from (Condition 2) above. Further, once the upper limit value of V is decided, the upper limit value of the length (H) of the first arm 707a can be decided from (Condition 1) above and the lower limit value of the length (T) of the prop unit 707c can be decided from (Condition 3) above. Moreover, the upper limit value of the length (T) of the prop unit 707c can also be decided from (Condition 7) above. The specific values of H, V, and T are decided within the decided ranges of H, V, and T such that (Condition 4) to (Condition 6) above are satisfied.

The present inventors have actually designed the support unit 703 on the assumption that the height (B) of the operating table 740 of (Condition 7) above is 800 (mm), and the horizontal required arrival distance (WH) and the vertical required arrival distance (WV) of (Condition 4) above are WH=800 (mm) and WV=1600 (mm). As a result, it is revealed that the length (H) of the first arm 707a, the length (V) of the second arm 707b, and the length (T) of the prop unit 707c generally satisfy the following relationships.

$H+V+T>$approximately 2000 (mm)

$H<T<V$ approximately 800 (mm)$<V<$approximately 1000 (mm)

approximately 600 (mm)$<H<$approximately 800 (mm)

Additionally, the above-described numeric value 2000 (mm) is calculated such that the minimum movable range required of the microscope unit 701 can be achieved. In a case where a wider movable range is obtained in consideration of margins, the lower limit value of H+V+T can be a larger value. For example, a result of consideration of the present inventors reveals that it is preferable to configure the support unit 703 such that H+V+T>approximately 2100 (mm) is satisfied, in a case where a wider movable range is achieved for the microscope unit 701 such that more various use modes can be covered. A result of further continuous consideration reveals that it is preferable to configure the support unit 703 such that, for example, H+V+T>approximately 2200 (mm) is satisfied, in order to move the microscope unit 701 at more degrees of freedom.

The result obtained by the present inventors actually designing the configuration of the support unit 703 which can satisfy each of the above-described conditions has been described above.

3. Configuration Example of Microscope Device

A specific configuration example of the microscope device according to the present embodiment which can satisfy (Condition 1) to (Condition 7) described above will be described with reference to FIG. 9. FIG. 9 is a diagram illustrating a configuration example of the microscope system according to the present embodiment.

Figure 9:
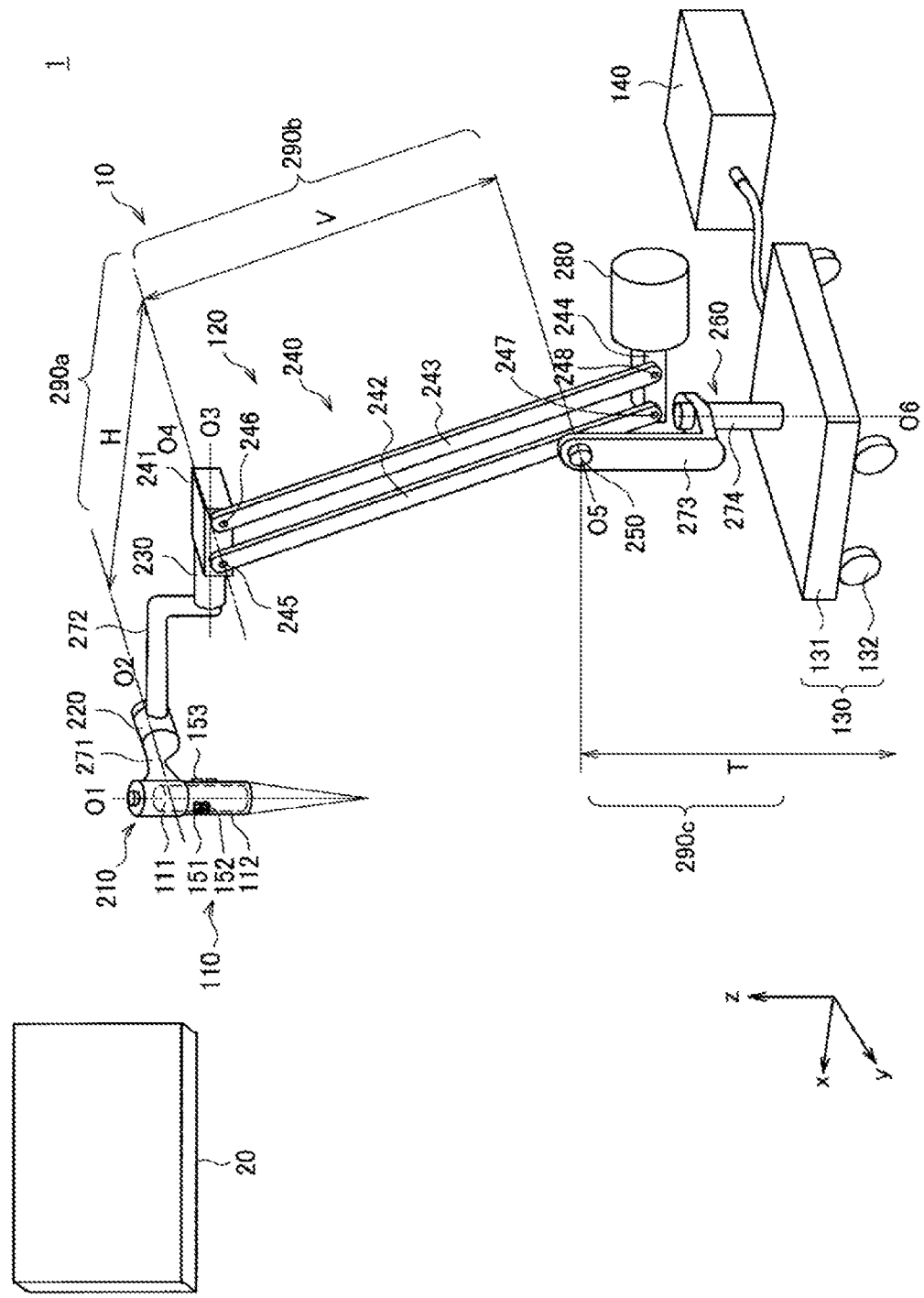
FIG. 9 is a diagram illustrating a configuration example of a microscope system according to the present embodiment.

FIG. 9 illustrates that a microscope system 1 according to the present embodiment includes a microscope device 10 that supports a microscope unit 110, and images an operative site of a patient with the microscope unit 110, and a display device 20 that displays an image of the operative site captured by the microscope device 10. A surgeon observes the operative site in an operation while referring to the image that is captured by the microscope device 10 and displayed on the display device 20, and applies a variety of treatments to the operative site.

(Display Device)
The display device 20 displays an image of an operative site of a patient which is captured by the microscope device 10 as described above. The display device 20 is installed in a place such as a wall of an operating room that can be visually recognized by a surgeon. The type of the display device 20 is not limited in particular. Various known display devices such as a cathode ray tube (CRT) display device, a liquid crystal display device, a plasma display device, and an electro-luminescence (EL) display device may be used as the display device 20. Additionally, as described below, in a case where an imaging unit 111 is configured as a stereo camera, and/or a case where the imaging unit 111 is compatible with high-resolution imaging, display devices that are respectively capable of 3D display and/or high-resolution display can be used as the display device 20. Further, the display device 20 does not necessarily have to be installed in an operating room, but may be mounted on a device that is worn and used by a surgeon like a head-mounted display (HMD) or a glasses-type wearable device.

(Microscope Device)

The microscope device 10 includes the microscope unit 110 for the magnified observation of an operative site of a patient, the support unit 120 (arm unit 120) that holds the microscope unit 110, a base unit 130 that is connected to an end of the support unit 120 and supports the microscope unit 110 and the support unit 120, and a control device 140 that controls the operation of the microscope device 10. The microscope device 10 is a surgical microscope device for the magnified observation of an operative site of a patient in an operation.

(Base Unit 130)

The base unit 130 supports the microscope unit 110 and the support unit 120. The base unit 130 includes a stand 131 shaped like a plate, and casters 132 provided to the bottom of the stand 131. An end of the support unit 120 is connected to the top of the stand 131, and the microscope unit 110 is connected to the other end (distal end) of the support unit 120 extending from the stand 131. Further, the microscope device 10 is grounded on the floor via the casters 132, and configured to be movable on the floor via the casters 132.

(Microscope Unit 110)

The microscope unit 110 includes a microscopic mirror body for the magnified observation of an operative site of a patient. In the illustrated example, the optical axis direction of the microscope unit 110 substantially agrees with the z-axis direction. The microscope unit 110 includes a barrel unit 112 that has the configuration corresponding to that of the electronic imaging microscope and is shaped substantially like a cylinder, and the imaging unit 111 provided in the barrel unit 112. Further, the imaging unit 111 includes an optical system such as an objective lens and a zoom lens, and an image sensor that captures an image of an object (i.e., operative site) with light passing through the optical system. Additionally, the length of the microscope unit 110 (more strictly, the length from the connection portion of a first arm 290a described below and the microscope unit 110 to the lower end of the microscope unit 110) in the optical axis direction is, for example, approximately 210 mm or shorter, more preferably approximately 200 mm or shorter.

The aperture at the lower end of the barrel unit 112 is provided with a cover glass that protects the imaging unit 111. There is also provided a light source in the barrel unit 112. When an image is captured, the light source irradiates an object with illumination light through the cover glass. The illumination light reflected by the object is incident on the imaging unit 111 via the cover glass, and the imaging unit 111 acquires a signal (image signal) for an image of an operative site.

Various known components corresponding to the electronic imaging microscope unit may be applied as the microscope unit 110. Accordingly, the detailed description thereof will not be made here. For example, various known image sensors such as a charge coupled device (CCD) sensor and a complementary metal-oxide-semiconductor (CMOS) sensor may be applied as the image sensor of the imaging unit 111. Further, the imaging unit 111 may also be configured as a so-called stereo camera including a pair of image sensors. In this case, an image captured by the imaging unit 111 can be three-dimensionally displayed. Further, the imaging unit 111 may be configured to compatible with high-definition imaging such as 4K or more (e.g., 4K (the number of horizontal pixels 3840×the number of vertical pixels 2160), 8K (the number of horizontal pixels 7680×the number of vertical pixels 4320), or the like). In this case, the state of an operative site can be more clearly displayed on the display device 20, which enables an operation to be smoothly performed. Additionally, in a case where the imaging unit 111 is compatible with high-resolution imaging, the use of a 55-inch or larger display device as the display device 20 offers a still stronger sense of immersion. Further, various known components can also be applied to the optical system of the imaging unit 111. Moreover, the imaging unit 111 can have the typical various functions of the electronic imaging microscope unit like an auto focus (AF) function, an optical zoom function, and the like.

The image signal acquired by the microscope unit 110 is transmitted to the control device 140, and the control device 140 performs various kinds of image processing such as gamma correction or white balance adjustment. Further, the control device 140 may further perform image processing such as magnification with the electronic zoom function or inter-pixel correction. The image signal subjected to the image processing is transmitted to the display device 20 provided in an operating room, and the image of the operative site is magnified and displayed as appropriate on the display device 20 at a desired magnification, for example, by using the optical zoom function and/or the electronic zoom function. Additionally, the communication between the control device 140 and the display device 20 may be established in various known wired or wireless schemes.

Additionally, the microscope unit 110 may include a processing circuit for performing the above-described image processing, and the above-described image processing may be performed not by the control device 140, but by the processing circuit of the microscope unit 110. In this case, image information subjected to image processing as necessary by the processing circuit included in the microscope unit 110 can be transmitted from the microscope unit 110 to the display device 20 provided in the operating room. Further, in this case, the communication between the microscope unit 110 and the display device 20 may be established in various known wired or wireless schemes.

The microscope unit 110 includes a variety of switches for controlling the operation of the microscope unit 110. For example, the microscope unit 110 includes a zoom switch 151 (zoom SW 151) and a focus switch 152 (focus SW 152) for adjusting an imaging condition of the microscope unit 110, and an operation mode change switch 153 (operation mode change SW 153) for changing the operation mode of the support unit 120.

A surgeon can respectively adjust the magnification and the focal distance of the microscope unit 110 by operating the zoom SW 151 and the focus SW 152. Further, the surgeon can switch the operation mode of the support unit 120 to any of a fixation mode and a free mode by operating the operation mode change SW 153.

Here, the fixation mode is an operation mode in which the rotation around each rotation axis provided to the support unit 120 is regulated by a brake, and the position and the attitude of the microscope unit 110 are hereby fixed. The free mode is an operation mode in which releasing the brake allows for free rotation around each rotation axis provided to the support unit 120, and the position and the attitude of the microscope unit 110 can be adjusted through a direct operation of a surgeon. Here, the direction operation means an operation of a surgeon to grasp the microscope unit 110, for example, with a hand, and directly move the microscope unit 110. For example, while a surgeon is pushing down the operation mode change SW 153, the operation mode of the support unit 120 is the free mode. While a surgeon keeps his or her hand from the operation mode change SW 153, the operation mode of the support unit 120 is the fixation mode.

Additionally, these switches do not necessarily have to be provided to the microscope unit 110. As long as the microscope device 10 is provided with a mechanism that has an equivalent function to those of these switches and receives an operation input, the specific configuration of the mechanism is not limited in the present embodiment. For example, these switches may be provided to other parts of the microscope device 10. Further, for example, the corresponding instructions to these switches may be remotely input into the microscope device 10 by using an input device such as a remote controller.

Further, FIG. 9 simplifies the barrel unit 112 of the microscope unit 110 as a simple cylinder-shaped member for the sake of simplicity, but the barrel unit 112 may actually vary in shape to be easy for a surgeon to grasp. For example, the operation is possible that a surgeon moves the microscope unit 110 by directly grasping the barrel unit 112 with his or her hand when the free mode is set. The surgeon then performs an operation of moving the microscope unit 110 while pushing down the operation mode change SW 153. Accordingly, the shape of the barrel unit 112 and the disposition of the operation mode change SW 153 can be decided as appropriate in consideration of the operability of the surgeon when the free mode is set. Further, the disposition of the zoom SW 151 and the focus SW 152 may also be similarly decided as appropriate in consideration of the operability of the surgeon.

(Control Device 140)

The control device 140 includes processors such as a central processing unit (CPU) and a digital signal processor (DSP), a control board on which these processors, a storage element, and the like are mounted together, or the like. The control device 140 executes the operational processing that complies with a predetermined program, thereby controlling the operation of the microscope device 10.

For example, the control device 140 has a function of switching the above-described operation mode of the support unit 120 by controlling the driving of a brake provided to each joint unit of the support unit 120 in accordance with an operation input made by a surgeon via the above-described operation mode change SW 153. Further, for example, the control device 140 has a function of driving the optical system of the imaging unit 111 of the microscope unit 110 as appropriate in accordance with an operation input made by a surgeon via the above-described zoom SW 151 and focus SW 152 to adjust the magnification and the focal distance of the microscope unit 110. Further, the control device 140 has a function of performing various kinds of image processing on the image signal captured by the microscope unit 110, and transmitting the processed image signal to the display device 20 provided in an operating room.

Additionally, the control device 140 is provided as a different component from the microscope unit 110, the support unit 120, and the base unit 130, and connected to the base unit 130 by a cable in the illustrated example, but the present embodiment is not limited to such an example. For example, a processor, a control board, or the like that executes a similar function to that of the control device 140 may be disposed in the base unit 130. Further, the control device 140 may be integrated with the microscope unit 110 by incorporating the processor, the control board, or the like that executes the similar function to that of the control device 140 into the microscope unit 110.

(Support Unit 120)

The support unit 120 holds the microscope unit 110, three-dimensionally moves the microscope unit 110, and fixes the position and the attitude of the moved microscope unit 110. The support unit 120 is configured as a balance arm having six degrees of freedom in the present embodiment. The present embodiment is not, however, limited to such an example. The support unit 120 may be configured to have different degrees of freedom. Configuring the support unit 120 as a balance arm such that the microscope unit 110 and the support unit 120 have a balanced moment as a whole makes it possible to move the microscope unit 110 with smaller external force. Accordingly, it is possible to further improve the operability of a surgeon.

The support unit 120 is provided with six rotation axes (a first axis $O_1$, a second axis $O_2$, a third axis $O_2$, a fourth axis $O_4$, a fifth axis $O_5$, and a sixth axis $O_6$) corresponding to six degrees of freedom. The following describes and refers to members for the respective rotation axes as rotary shafts all together for the sake of convenience. For example, a rotary shaft can include a bearing, a shaft pivotably inserted through the bearing, a brake that regulates the rotation around the rotation axis, and the like. A parallelogram link mechanism 240 described below can also be considered one of the rotary shafts.

The support unit 120 includes a first rotary shaft 210, a second rotary shaft 220, a third rotary shaft 230, a fourth rotary shaft 240, a fifth rotary shaft 250 and a sixth rotary shaft 260 that correspond to the respective rotation axes, a first arm unit 271, a second arm unit 272, a third arm unit 273 and a fourth arm unit 274 that are pivotably connected to each other by these first rotary shaft 210 to sixth rotary shaft 260, and a counterweight 280 that allows the microscope unit 110 and the support unit 120 to have a balanced moment as a whole. However, the fourth rotary shaft 240 corresponds to the parallelogram link mechanism 240.

The first rotary shaft 210 is shaped substantially like a cylinder, and connected to the proximal-end part of the barrel unit 112 of the microscope unit 110 such that the central axis thereof substantially agrees with the central axis of the barrel unit 112 of the microscope unit 110. The first rotary shaft 210 pivotably supports the microscope unit 110 by using, as a rotation axis direction (first axis $O_1$ direction), the direction that substantially agrees with the optical axis of the microscope unit 110. The first axis $O_1$ is provided as a rotation axis substantially parallel to the z axis in the example illustrated in FIG. 9. The first rotary shaft 210 pivots the microscope unit 110 on the first axis $O_1$, thereby adjusting the direction of a captured image by the microscope unit 110.

Additionally, a part of the imaging unit 111 of the microscope unit 110 is stored in a cylinder-shaped housing included in the first rotary shaft 210 in the illustrated example. That is, the microscope unit 110 and the first rotary shaft 210 are configured as an integrated member. The present embodiment is not, however, limited to such an example. The first rotary shaft 210 and the microscope unit 110 may also be configured as different members.

The first rotary shaft 210 is connected to the distal end of the first arm unit 271 extending in the direction substantially perpendicular to the first axis $O_1$. Further, the proximal end of the first arm unit 271 is provided with the second rotary shaft 220 that pivotably supports the first arm unit 271 by using, as a rotation axis direction (second axis $O_2$ direction), the direction substantially parallel to the extending direction of the first arm unit 271. The second axis $O_2$ is a rotation axis substantially perpendicular to the first axis $O_1$, and provided as a rotation axis substantially parallel to the y axis in the example illustrated in FIG. 9. The second rotary shaft 220 pivots the microscope unit 110 and the first arm unit 271 by using the second axis $O_2$ as a rotation axis, thereby adjusting the position of the microscope unit 110 in the x-axis direction.

The second rotary shaft 220 is connected to the distal end of the second arm unit 272 extending in the direction substantially perpendicular to the first axis $O_1$ and the second axis $O_2$. Further, the proximal-end side of the second arm unit 272 is wound substantially like the letter L, and the third rotary shaft 230 is provided at the position corresponding to the shorter side of the bent portion. The third rotary shaft 230 pivotably supports the second arm unit 272 by using, as a rotation axis direction (third axis $O_3$ direction), the direction substantially parallel to the extending direction of the part of the second arm unit 272 corresponding to the longer side. The third axis $O_3$ is a rotation axis substantially perpendicular to the first axis $O_1$ and the second axis $O_2$, and provided as a rotation axis substantially parallel to the x axis in the example illustrated in FIG. 9. The third rotary shaft 230 pivots the microscope unit 110, the first arm unit 271, and the second arm unit 272 by using the third axis $O_3$ as a rotation axis, thereby adjusting the position of the microscope unit 110 in the y-axis direction.

The support unit 120 is configured such that the attitude of the microscope unit 110 is controlled by controlling the rotations around the second axis $O_2$ and the third axis $O_3$ in this way. That is, the second rotary shaft 220 and the third rotary shaft 230 can be rotary shafts that define the attitude of the microscope unit 110.

The proximal-end side of the third rotary shaft 230 is connected to the distal end of the upper side of the parallelogram link mechanism 240. The parallelogram link mechanism 240 includes four arms (arms 241, 242, 243, and 244) disposed in the shape of a parallelogram, and four joint unit (joint units 245, 246, 247, and 248) provided at the respective positions substantially corresponding to the apexes of the parallelogram.

The third rotary shaft 230 is connected to the distal end of the arm 241 extending in the direction substantially parallel to the third axis $O_3$. The joint unit 245 and the joint unit 246 are respectively provided near the distal end and the proximal end of the arm 241. The joint units 245 and 246 are respectively connected to the distal ends of the arms 242 and 243 rotatably around the rotation axes (fourth axis $O_4$) that are substantially perpendicular to the extending direction of the arm 241 and substantially parallel to each other. Moreover, the joint units 247 and 248 are respectively provided to the proximal ends of the arms 242 and 243. These joint units 247 and 248 are respectively connected to the distal end and proximal end of the arm 244 rotatably around the fourth axis $O_4$ and is substantially parallel to the arm 241.

In this way, the four joint units included in the parallelogram link mechanism 240 have the rotation axes (fourth axis $O_4$) that are substantially parallel to each other and have substantially the same direction, and operate around the fourth axes $O_4$ in conjunction with each other. The fourth axis $O_4$ is provided as a rotation axis substantially parallel to the y axis in the example illustrated in FIG. 9. That is, the parallelogram link mechanism 240 includes joint units that are disposed at different positions, and rotate in conjunction with each other around rotation axes that have the same direction, and the parallelogram link mechanism 240 serves as a transmission mechanism that transmits an operation at an end to the other end. If the parallelogram link mechanism 240 is provided, the movement of the components (i.e., the microscope unit 110, the first rotary shaft 210, the second rotary shaft 220, the third rotary shaft 230, the first arm unit 271, and the second arm unit 272) closer to the distal-end side than the parallelogram link mechanism 240 is transmitted to the proximal-end side of the parallelogram link mechanism 240.

The fifth rotary shaft 250 is provided to the portion a predetermined distance away from the proximal end of the arm 242. The fifth rotary shaft 250 pivotally supports the parallelogram link mechanism 240 by using, as a rotation axis direction (fifth axis $O_5$ direction), the direction perpendicular to the extending direction of the arm 242. The fifth axis $O_5$ is a rotation axis substantially parallel to the fourth axis $O_4$, and provided as a rotation axis substantially parallel to the y axis in the example illustrated in FIG. 9. The fifth rotary shaft 250 is connected to the distal end of the third arm unit 273 extending in the z-axis direction. The microscope unit 110, the first arm unit 271, the second arm unit 272, and the parallelogram link mechanism 240 are configured to be pivotable with respect to the third arm unit 273 via the fifth rotary shaft 250 by using the fifth axis $O_5$ as a rotation axis.

The third arm unit 273 is shaped substantially like the letter L. The proximal-end side thereof is bent to be substantially parallel to the floor. The surface of the third arm unit 273 substantially parallel to the floor is connected to the sixth rotary shaft 260 that can pivot the third arm unit 273 on a rotation axis (sixth axis $O_6$) orthogonal to the fifth axis $O_5$. The sixth axis $O_6$ is provided as a rotation axis substantially parallel to the z axis in the example illustrated in FIG. 9.

The sixth rotary shaft 260 is integrated with the fourth arm unit 274 extending in the vertical direction in the illustrated example. That is, the distal end of the fourth arm unit 274 is connected to the surface of the proximal end of the third arm unit 273 which is substantially parallel to the floor. Further, the proximal end of the fourth arm unit 274 is connected to the top of the stand 131 of the base unit 130. Configured in this way, the microscope unit 110, the first arm unit 271, the second arm unit 272, the parallelogram link mechanism 240, and the third arm unit 273 pivot with respect to the base unit 130 via the sixth rotary shaft 260 by using the sixth axis $O_6$ as a rotation axis.

The arm 244 included in the lower side of the parallelogram link mechanism 240 is shaped to be longer than the arm 241 included in the upper side of the parallelogram link mechanism 240, and the end of the arm 242 that is positioned diagonally to the part of the parallelogram link mechanism 240 to which the third rotary shaft 230 is connected extends to the outside of the parallelogram link mechanism 240. The counterweight 280 is provided to the extending end of the arm 244. The mass and disposition of the counterweight 280 are adjusted such that the rotation moment generated about the fourth axis $O_4$ and the rotation moment generated about the fifth axis $O_5$ can cancel each other out by the mass of each of the components (i.e., the microscope unit 110, the first rotary shaft 210, the second rotary shaft 220, the third rotary shaft 230, the first arm unit 271, the second arm unit 272, and the parallelogram link mechanism 240) disposed closer to the distal-end side than the counterweight 280.

Further, the disposition of the fifth rotary shaft 250 is adjusted such that the center of gravity of each of the components disposed closer to the distal-end side than the fifth rotary shaft 250 is positioned on the fifth axis $O_5$. Moreover, the disposition of the sixth rotary shaft 260 is adjusted such that the center of gravity of each of the components disposed closer to the distal-end side than the sixth rotary shaft 260 is positioned on the sixth axis $O_6$.

The mass and disposition of the counterweight 280, the disposition of the fifth rotary shaft 250, and the disposition of the sixth rotary shaft 260 are configured in this way, which can configure the support unit 120 as a balance arm that has a balanced moment between the microscope unit 110 and the support unit 120 as a whole. Configuring the support unit 120 as a balance arm allows a surgeon to move the microscope unit 110 with smaller external force as if the surgeon was under zero gravity in a case where the surgeon attempts to move the microscope unit 110 through a direct operation. It is thus possible to improve the operability of a user.

Additionally, the counterweight 280 may be attachable and detachable. For example, in a case where some types of counterweights 280 different in mass are prepared and the components disposed closer to the distal-end side than the parallelogram link mechanism 240 are changed, a counterweight 280 that can cancel the rotation moment may be selected as appropriate in accordance with the change.

The first rotary shaft 210 to the sixth rotary shaft 260 of the support unit 120 are respectively provided with brakes that regulate the rotations of the first rotary shaft 210 to the sixth rotary shaft 260. Additionally, the four joint units (joint units 245 to 248) of the parallelogram link mechanism 240 rotate in conjunction with each other. Accordingly, a brake for the parallelogram link mechanism 240 only has to be provided to at least any of these four joint units. The driving of these brakes is controlled by the control device 140. The control exerted from the control device 140 releases these brakes all at once. This causes the operation mode of the support unit 120 to transition to the free mode. Further, the control exerted from the control device 140 drives these brakes all at once. This causes the operation mode of the support unit 120 to transition to the fixation mode in the same way.

Additionally, a variety of brakes used for a typical balance arm may be applied as the brakes provided to the first rotary shaft 210 to the sixth rotary shaft 260. The specific mechanisms thereof are not limited. For example, these brakes may be mechanically driven, or may be electromagnetic brakes that are electrically driven.

Here, the component corresponding to from the first arm unit 271 to the joint unit 245 on the upper side (arm 241) of the parallelogram link mechanism 240 corresponds to the first arm 290a, the component corresponding to from the upper side (arm 241) of the parallelogram link mechanism 240 to the fifth rotary shaft 250 corresponds to a second arm 290b, and the component corresponding to from the fifth rotary shaft 250 to the proximal end of the fourth arm unit 274 corresponds to a prop unit 290c in the support unit 120 of the microscope device 10.

The support unit 120 is configured in the present embodiment such that these first arm 290a, second arm 290b, and prop unit 290c satisfy at least (Condition 1) (i.e., V>H) above. Further, the support unit 120 may also be configured such that other (Condition 2) to (Condition 7) are further satisfied. This can configure the microscope device 10 such that each advantageous effect as described in (2. Design Idea of Support Unit of Microscope Device according to the Present Embodiment) above is attained. Additionally, the length (T) of the prop unit 290c means the distance from the floor to the fifth rotary shaft 250 in the configuration illustrated in FIG. 9 in a discussion on these conditions.

The specific configuration example of the microscope device 10 according to the present embodiment has been described above with reference to FIG. 9. The configuration of the microscope device 10 according to the present embodiment is not, however, limited to such an example. As long as the microscope device 10 is configured such that each of the above-described conditions is satisfied, the microscope device 10 may adopt any specific configuration.

4. Use Examples of Microscope Device

Figure 10:
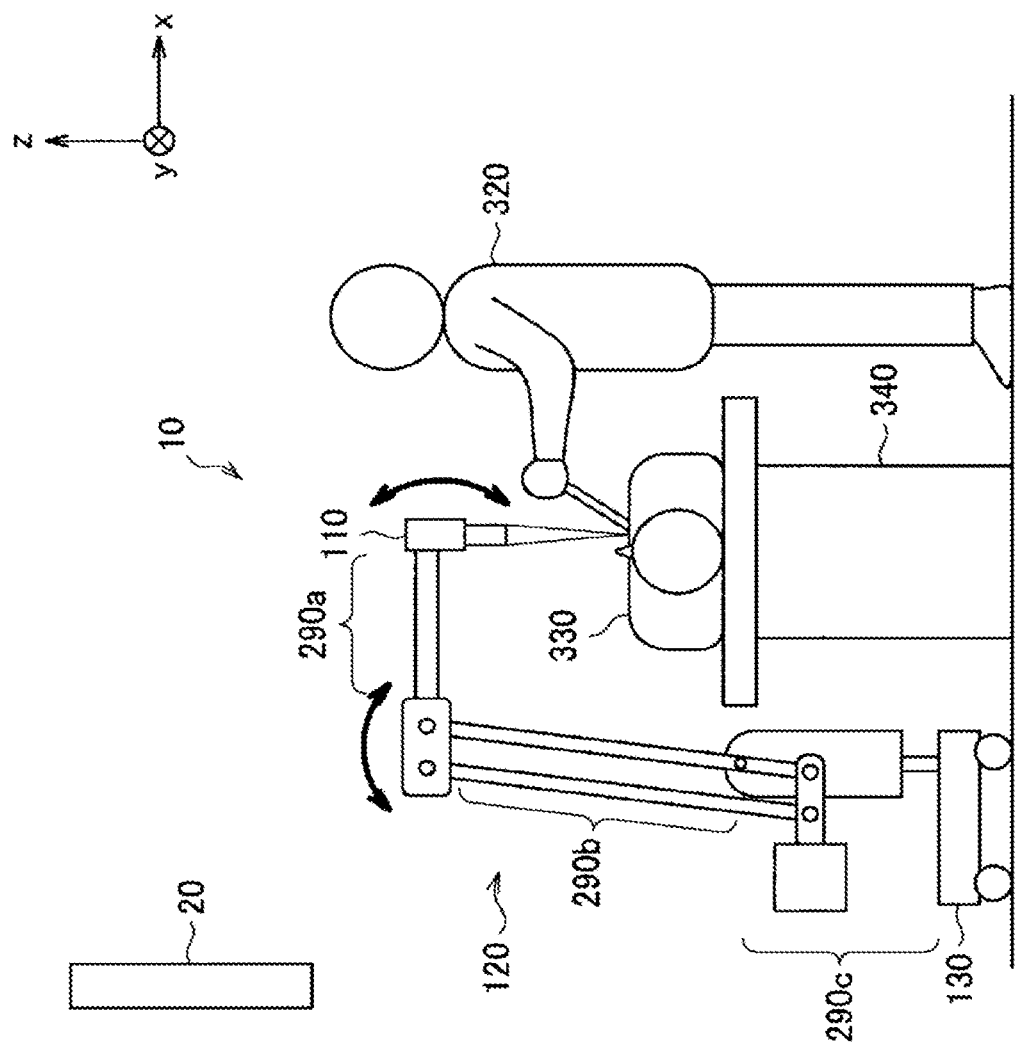
FIG. 10 is a diagram illustrating an operation using the microscope device according to the present embodiment at a standing position

Use examples of the above-described microscope device 10 will be described with reference to FIGS. 10 to 12. Additionally, FIGS. 10 to 12 simplify the microscope device 10 illustrated in FIG. 9 for the sake of simplicity.

4-1. Use Example in Operations at Standing Position

First, a use example of the microscope device 10 in operations at the standing position will be described with reference to FIG. 10. FIG. 10 is a diagram illustrating an operation using the microscope device 10 according to the present embodiment at the standing position FIG. 10 illustrates that a surgeon 320 uses the microscope device 10 to operate on a patient 330 lying down on an operating table 340 at the standing position. An image of an operative site of the patient 330 is captured by the microscope unit 110 of the microscope device 10, and the captured image of the operative site is displayed on the display device 20 in an operation. The surgeon 320 performs an operation while observing the image of the operative site shown on the display device 20.

Operations at the standing position are performed chiefly in departments such as orthopedics and cardiac surgery. The surgeon 320 is secured a relatively wide working space in many operations at the standing position. The microscope unit 110 for imaging an operative site is therefore disposed also at a relatively high position.

When an operation begins, the entire microscope device 10 is moved close to the operating table 340 by using the casters. The microscope device 10 is then disposed as close to the operating table 340 as possible. The configuration of the microscope device 10 can be configured to be small in the present embodiment. Accordingly, even if the microscope device 10 is disposed close to the operating table 340, the microscope device 10 is unlikely to interfere with the surgeon 320 or the like working. Further, the prop unit 290c of the microscope device 10 can be configured to have shorter length (T) than the height (B) of the operating table 340. Accordingly, even if the microscope device 10 is disposed close to the operating table 340, there is no risk that the clean area on the top of the operating table 340 is invaded. Additionally, the height (B) of the operating table 340 used in operations at the standing position is, for example, approximately 800 (mm).

Grasping a grip unit of the microscope unit 110, the surgeon 320 then pushes down the operation mode change SW 153 to release the brakes provided to the first rotary shaft 210 to the sixth rotary shaft 260 and set the free operation mode, in which the microscope unit 110 can be namely moved freely. While observing the image that is captured by the microscope unit 110 and displayed on the display device 20, the surgeon 320 moves the microscope unit 110 to allow the microscope unit 110 to bring the operative site into view.

The surgeon 320 then releases the operation mode change SW 153 (i.e., changes the operation mode into the fixation mode) to fix the attitudes of the microscope unit 110 and the support unit 120. At this time, the support unit 120 of the microscope device 10 can be configured such that the movable range of the microscope unit 110 satisfies a desired movable range. The surgeon 320 can therefore move the microscope unit 110 to a position at which a desired image is acquired.

Here, the microscope device 10 is configured such that the length (V) of the second arm 290b is greater than the length (H) of the first arm 290a. Accordingly, if the microscope device 10 is disposed close to the operating table 340 and the second arm 290b has a substantially perpendicular attitude, it is possible to dispose the microscope unit 110 at a higher position while keeping the first arm 290a substantially level. That is, it is possible to dispose the microscope unit 110 in a use area in an operation at the standing position. Further, since the first arm 290a is kept substantially level, it is possible to prevent the first arm 290a from interfering with the working space of the surgeon 320 and the view of the surgeon 320, and favorably secure the working space and the view. In this way, if the support unit 120 is configured such that the length (V) of the second arm 290b is greater than the length (H) of the first arm 290a, the microscope device 10 makes it possible to secure the working space of the surgeon 320 and the view of the surgeon 320 while disposing the microscope unit 110 at a higher position at which a sufficient working space can be secured in an operation at the standing position.

The surgeon 320 operates the zoom SW 151 and the focus SW 152 with the attitudes of the microscope unit 110 and the support unit 120 fixed, and adjusts the magnification and the focal distance of an image captured by the microscope unit 110. The surgeon 320 begins treatment while observing the adjusted image.

The use example of the microscope device 10 in operations at the standing position have been described above with reference to FIG. 10.

4-2. Use Example in Operations at Seated Position

Next, a use example of the microscope device 10 in operations at the seated position will be described with reference to FIG. 11. FIG. 11 is a diagram illustrating an operation using the microscope device 10 according to the present embodiment at the seated position.

Figure 11:
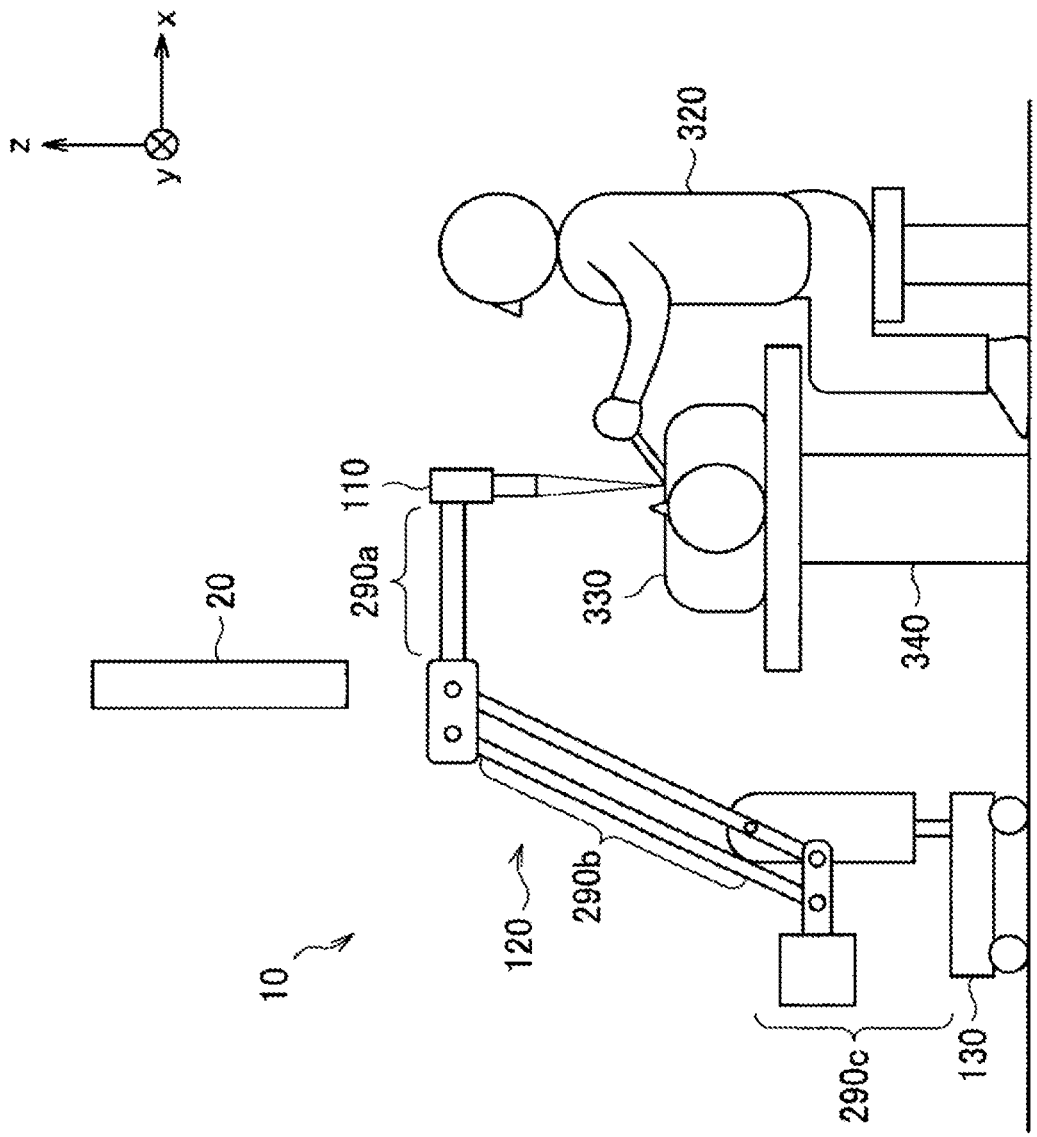
FIG. 11 is a diagram illustrating an operation using the microscope device according to the present embodiment at a seated position.

FIG. 11 illustrates that the surgeon 320 uses the microscope device 10 to operate on the patient 330 lying down on the operating table 340 at the seated position. Additionally, operations at the seated position are different from operations at the standing position only in the disposition of the microscope device 10 and the attitude of the support unit 120, but the other procedures in operations at the seated position are similar to those in operations at the standing position. What is common to operations at the standing position will not be thus described in detail, but what is different will be chiefly described in the following description of a use example of the microscope device 10 in operations at the seated position.

Operations at the seated position are performed chiefly in departments such as neurosurgery. The surgeon 320 performs an operation at the seated position while seated. Accordingly, the height (B) of the operating table 340 is lower than that of a case of the standing position, and the microscope unit 110 that images an operative site is also disposed at a relatively low position. That is, the position of the use area of the microscope unit 110 in operations at the seated position is lower than that of the use area of the microscope unit 110 in operations at the standing position. Additionally, the height (B) of the operating table 340 used in operations at the seated position is, for example, approximately 600 (mm).

When an operation begins, the entire microscope device 10 is moved close to the operating table 340 by using the casters. The microscope device 10 is then disposed at a position farther from the operating table 340 than the position in operations at the standing position.

Similarly to operations at the standing position, the surgeon 320 then moves the microscope unit 110 to allow the microscope unit 110 to bring an operative site into view, while observing the display device 20, and fixes the attitudes of the microscope unit 110 and the support unit 120. Here, the microscope device 10 is configured such that the length (V) of the second arm 290b is greater than the length (H) of the first arm 290a. Accordingly, if the microscope device 10 is disposed at a position far from the operating table 340 and the attitude of the support unit 120 is adjusted such that the second arm 290b is inclined toward the operating table 340, it is possible to dispose the microscope unit 110 at a lower position which is namely the position corresponding to the use area in operations at the seated position while keeping the first arm 290a substantially level.

According to the present embodiment, the support unit 120 is configured in this way such that the length (V) of the second arm 290b is greater than the length (H) of the first arm 290a. Accordingly, if the distance between the microscope device 10 and the operating table 340 (i.e., distance between the prop unit 290c and the operating table 340) is adjusted as appropriate, it is possible to dispose the microscope unit 110 at different heights while keeping the first arm 290a substantially level. It is thus possible to cover both operations at the standing position and operations at the seated position, which are different in the height of the use area. It is possible to keep the first arm 209a substantially level in any of operations at the standing position and operations at the seated position, which can secure the working space of the surgeon 320 and the view of the surgeon 320 regardless of the operation modes.

The surgeon 320 operates the zoom SW 151 and the focus SW 152 once the attitudes of the microscope unit 110 and the support unit 120 are fixed, and adjusts the magnification and the focal distance of an image captured by the microscope unit 110. The surgeon 320 begins treatment while observing the adjusted image.

The use example of the microscope device 10 in operations at the seated position has been described above with reference to FIG. 11.

Figure 12:
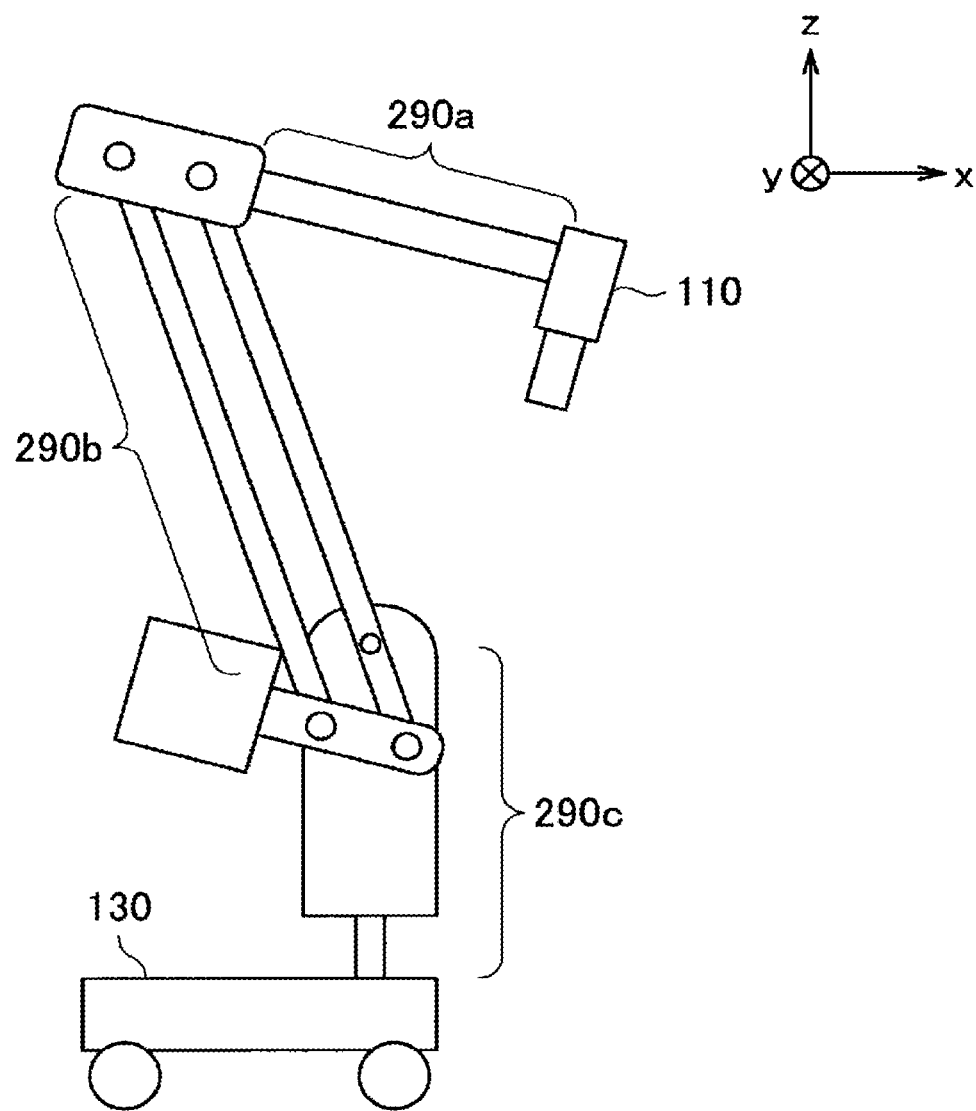
FIG. 12 is a diagram illustrating an example of a state of the stored microscope device according to the present embodiment.

Additionally, in a case where the microscope device 10 is not used for any operation, namely when stored, the microscope device 10 is stored in a predetermined space with the support unit 120 folded (the first arm 707a is rotated toward the second arm 707b as much as possible) as illustrated in FIG. 12. FIG. 12 is a diagram illustrating an example of the state of the stored microscope device 10 according to the present embodiment. Since the microscope device 10 is configured such that the length (V) of the second arm 707b is greater than the length (H) of the first arm 707a, the support unit 120 is configured to be relatively long in height (length in the vertical direction) and relatively short in width (length in the horizontal direction). It is thus possible to further reduce the width of the support unit 120 by folding the support unit 120, and store the microscope device 10 in a small space.

5. Modifications

Some modifications of the above-described embodiment will be described.

5-1. Modification in Which Rotary Shaft is Added to Support Unit

Figure 13:
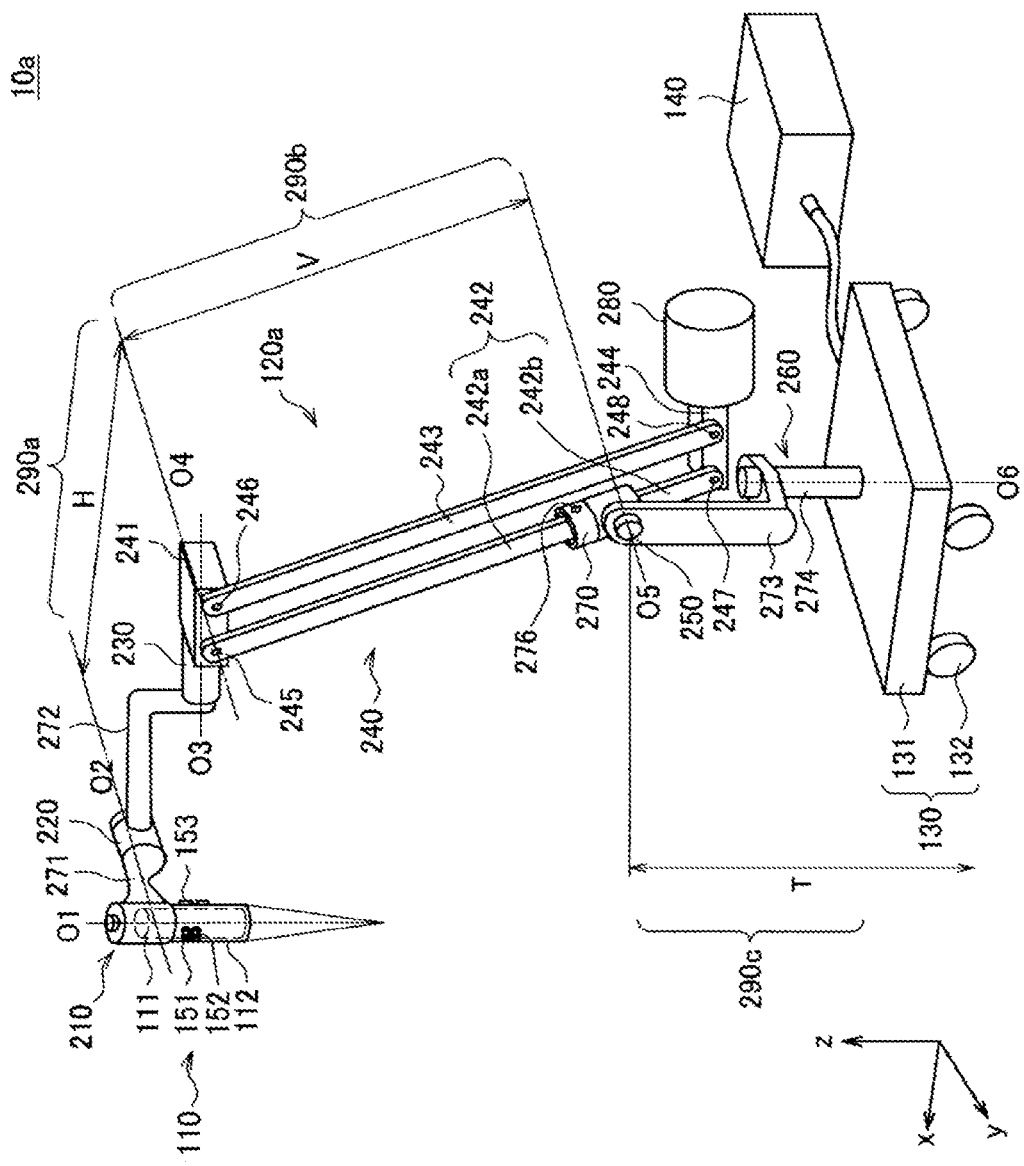
FIG. 13 is a diagram illustrating a configuration example of a microscope device according to a modification in which a rotary shaft is added to a support unit.

The configuration of a microscope device according to a modification in which a rotary shaft is added to a support unit will be described with reference to FIG. 13. FIG. 13 is a diagram illustrating a configuration example of the microscope device according to the modification in which a rotary shaft is added to the support unit. Additionally, the microscope device according to the present modification illustrated in FIG. 13 corresponds to the microscope device 10 which is described with reference to FIG. 9 and to which a seventh rotary shaft 270 described below is added. What is common to the above-described embodiment will not be thus described in detail, but only what is different will be chiefly described in the following description of the present modification.

FIG. 13 illustrates that a microscope device 10a according to the present modification corresponds to the microscope device 10 that is illustrated in FIG. 9, and provided with a further rotation axis (seventh axis $O_7$) other than the first axis $O_1$ to the sixth axis $O_6$. Specifically, the arm 242 of the parallelogram link mechanism 240 extending substantially in the vertical direction is divided into two members (arm 242a and arm 242b) in the extending direction thereof in a support unit 120a of the microscope device 10a. The seventh rotary shaft 270 is then provided between the proximal end of the arm 242a included in the distal-end side of the arm 242 and the distal end of the arm 242b included in the proximal-end side of the arm 242. The seventh rotary shaft 270 uses the extending direction of the arm 242 as a rotation axis direction (seventh axis $O_7$).

In this way, the microscope device 10a according to the present modification corresponds to the microscope device 10 according to the above-described embodiment which is provided with the seventh rotary shaft 270 at the position corresponding to the connection portion of the second arm 290b and the prop unit 290c.

The seventh rotary shaft 270 supports the arm 242a such that the arm 242a can pivot with respect to the arm 242b. The seventh rotary shaft 270 rotates the arm 242a around the seventh axis $O_7$, thereby operating the arm 242 such that the arm 242 twists along the extending direction thereof. That is, the seventh rotary shaft 270 is a rotary shaft that supports the second arm 290b rotatably around the rotation axis parallel to the extending direction of the second arm 290b. The seventh rotary shaft 270 operates the components on the second arm 290b closer to the distal end than the portion where the seventh rotary shaft 270 is provided, and the first arm 290a such that the components on the second arm 290b closer to the distal end than the portion where the seventh rotary shaft 270 is provided, and the first arm 290a twist along the extending direction of the second arm 290b.

A brake provided to the seventh rotary shaft 270 can be always in operation regardless of any operation on the operation mode change SW 153 in the present modification. In a case where an operation is performed in the normal procedure as described in (4-1. Use Example in Operations at Standing Position) and (4-2. Use Example in Operations at Seated Position) above, the seventh rotary shaft 270 does not thus rotate.

The seventh rotary shaft 270 is provided with a seventh shaft operation switch 276 (seventh shaft operation SW 276) for operating the brake of the seventh rotary shaft 270. The seventh shaft operation SW 276 is then pushed down by a surgeon, thereby releasing the brake of the seventh rotary shaft 270. For example, if a surgeon rotates the first arm 290a and/or the second arm 290b around the seventh axis $O_7$ in the fixation mode while pushing down the seventh shaft operation SW 276, the surgeon can change the attitude of the support unit 120a as appropriate with the position of the microscope unit 110 fixed.

For example, if the disposition of the microscope unit 110 is decided in an operation, some attitude of the support unit 120a causes the first arm 290a to interfere with a surgeon observing the display device 20 or causes the second arm 290b to be disposed close to a surgeon and interfere with the surgeon in some cases. In such a case, the surgeon operates the seventh shaft operation SW 276 to rotate the arm 242a around the seventh axis $O_7$ and move the components on the distal-end side of the second arm 290b and the first arm 290a in a twisting manner, and the surgeon can hereby change the positions of the second arm 290b and the first arm 290a such that the second arm 290b and the first arm 290a do not interfere with the surgeon. The surgeon releases his or her hand from the seventh shaft operation SW 276 and fixes the seventh rotary shaft 270 after finishing moving the second arm 290b and the first arm 290a. This fixes the attitude of the support unit 120a, and the surgeon can begin treatment for an operative site.

The configuration of the microscope device 10a according to the modification in which the rotary shaft (seventh rotary shaft 270) is added to the support unit 120a has been described above with reference to FIG. 13. As described above, according to the present modification, it is possible to move the microscope unit 110 to allows the microscope unit 110 to bring an operative site into view, and change the attitude of the support unit 120a as necessary and appropriate after the disposition of the microscope unit 110 is decided, such that the support unit 120a does not interfere with a surgeon. The microscope device 10a can be thus provided that is more convenient for the surgeon.

5-2. Modification in Which Electrical Unit is Mounted on Base Unit

Figure 14:
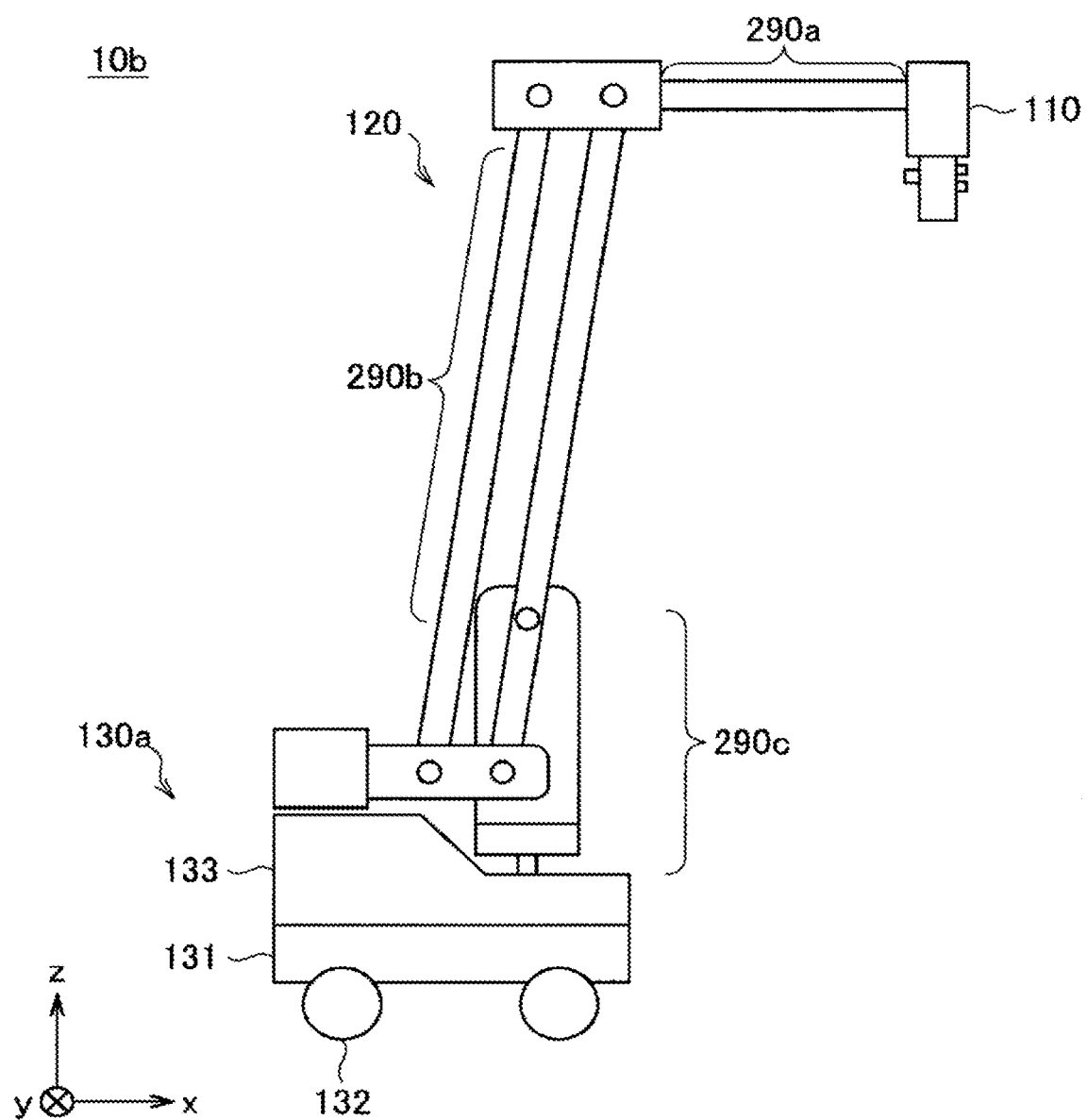
FIG. 14 is a diagram illustrating a configuration example of a microscope device according to a modification in which an electrical unit is added to a base unit.

The configuration of a microscope device according to a modification in which an electrical unit is mounted on a base unit will be described with reference to FIG. 14. FIG. 14 is a diagram illustrating a configuration example of the microscope device according to the modification in which the electrical unit is added to the base unit. Additionally, the microscope device according to the present modification illustrated in FIG. 14 corresponds to the microscope device 10 which is described with reference to FIG. 9 and to which an electrical unit 133 described below is added. What is common to the above-described embodiment will not be thus described in detail, but only what is different will be chiefly described in the following description of the present modification. Additionally, FIG. 14 simplifies the configuration of the microscope device like FIGS. 10 to 12 for the sake of simplicity.

FIG. 14 illustrates that a microscope device 10b according to the present modification corresponds to the microscope device 10 that is illustrated in FIG. 9 and includes the base unit 130 which is differently configured. Specifically, a base unit 130a of the microscope device 10b includes the stand 131 shaped like a plate, the casters 132 provided to the bottom of the stand 131, and the electrical unit 133 mounted on the top of the stand 131.

The electrical unit 133 includes, for example, a control board and the like. The electrical unit 133 has a similar function to the function of the control device 140 in the microscope device 10 illustrated in FIG. 9. That is, it can be said that the microscope device 10b corresponds to the control device 140 that is illustrated in FIG. 9 and integrated with the base unit 130a. The electrical unit 133 can execute various kinds of processing such as controlling the brake of each rotary shaft, controlling the driving of the imaging unit 111 in the microscope unit 110, and/or performing signal processing (i.e., image processing) on an image signal acquired by the microscope unit 110 which is performed by the control device 140 in the above-described embodiments.

Here, the electrical unit 133 is configured to be relatively high on the back side of the stand 131 (side of the support unit 120 provided with a counterweight), and relatively low on the front side of the stand 131 (side of the support unit 120 provided with the microscope unit 110). The prop unit 290c of the microscope device 10b is disposed at the portion on the front side of the stand 131, where the electrical unit 133 is lower, such that the proximal end is connected to the top of the electrical unit 133. That is, the proximal end of the prop unit 290c can be connected to the further front side of the stand 131 in the microscope device 10b as compared with the above-described embodiments. Additionally, although the electrical unit 133 is provided to the entire surface of the stand 131 in the illustrated configuration example, the electrical unit 133 may be provided to only the back side of the stand 131 and the proximal end of the prop unit 290c may be directly connected to the top of the stand 131 on the front side of the stand 131.

When an operation is performed with the microscope device 10b, this configuration disposes the prop unit 290c closer to an operating table than the configuration does in which the proximal end of the prop unit 290c is connected substantially to the center of the top of the stand 131. The first arm 290a is thus allowed to have shorter length (H), and it is possible to further miniaturize the device.

Further, if the electrical unit 133 that executes the functions of the control device 140 is mounted on the base unit 130a, it is unnecessary to separate the control device 140 from the base unit 130 like the configuration illustrated in FIG. 9, and it is possible to miniaturize the configuration of the microscope device 10b. The base unit 130a is configured such that the prop unit 290c is moved to the front side of the stand 131 and many of the components of the electrical unit 133 are mounted on the back side, which is a vacant area, at this time. Accordingly, the height of the support unit 120 is not substantially changed as compared with the above-described embodiments. That is, mounting the electrical unit 133 on the base unit 130a does not cause the device to be larger, but it is possible to efficiently miniaturize the configuration of the microscope device 10b.

Moreover, the base unit 130a can be a component belonging to an unclean area, but the electrical unit 133 is configured to be relatively high on the back side of the stand 131 and relatively low on the front side of the stand 131. This allows the electrical unit 133 that is an unclean area to be farther from the top of the operating table, namely a clean area. It is thus possible to mount the electrical unit 133 on the base unit 130a without increasing the risk that the clean area is invaded.

5-3. Modification in Which Prop Unit is Configured to Have Greater Length (T)

5-3-1. Overview of Microscope Device

The view of a surgeon is secured in the above-described embodiments by configuring the support unit 120 of the microscope device 10 such that the microscope unit 110 can be positioned below the display device 20 in an operation with the first arm 290a kept substantially level. The present embodiment is not, however, limited to such an example. For example, the support unit 120 may be configured such that the microscope unit 110 can be positioned above the display device 20 in an operation. Even in this case, the microscope unit 110 does not exist at the position at which the view of a surgeon watching the display device 20 is obstructed. Accordingly, it is possible to attain the advantageous effect similar to that of the above-described embodiments that the view of the surgeon is not obstructed, but the surgeon can clearly observe an operative site.

The microscope unit 110 can also be prevented from obstructing the view of a surgeon, by configuring the support unit 120 like the above-described embodiments such that the microscope unit 110 can be positioned below the display device 20. The microscope unit 110 is, however, positioned closer to the hands of the surgeon. Accordingly, some surgical procedures can cause the microscope unit 110 and the support unit 120 to interfere with the working space of the surgeon. In contrast, configuring the support unit 120 as described above such that the microscope unit 110 can be positioned above the display device 20 makes it more difficult for the microscope unit 110 and the support unit 120 to interfere with the working space of the surgeon. It can be then possible to further improve the convenience of the surgeon.

The above-described configuration of the support unit 120 can be achieved by increasing the length (T) of the prop unit 290c in the microscope device 10 according to the above-described embodiments. This allows the microscope unit 110 to be disposed at a higher position. Here, the microscope unit 110 is an electronic imaging microscope unit, and the position thereof is not restrained unlike an optical microscope unit that is made on the assumption of the use mode in which a surgeon directly looks through the ocular unit. Accordingly, if the focal distance is increased, the WD can be longer than that of the optical microscope unit. It is thus possible to observe an operative site even in a case where the microscope unit 110 is disposed at a higher position like this. The microscope unit 110 includes the electronic imaging microscope unit 110, and it is thus possible to configure the support unit 120 such that the microscope unit 110 can be positioned above the display device 20 in this way.

Here, such a microscope device including the support unit 120 configured such that the length (T) of the prop unit 290c is increased, and the microscope unit 110 can be hereby positioned above the display device 20 in an operation will be described as a modification of the present embodiment.

5-3-2. Schematic Configuration of Microscope Device

The configuration of the microscope device according to the present modification will be described. Additionally, the configuration of the microscope device according to the present modification is similar to the configuration of the microscope device 10 according to the above-described embodiments except that the length (T) of the prop unit 290c is increased. What is common will not be thus described in the following description of the configuration of the microscope device according to the present modification.

Figure 15:
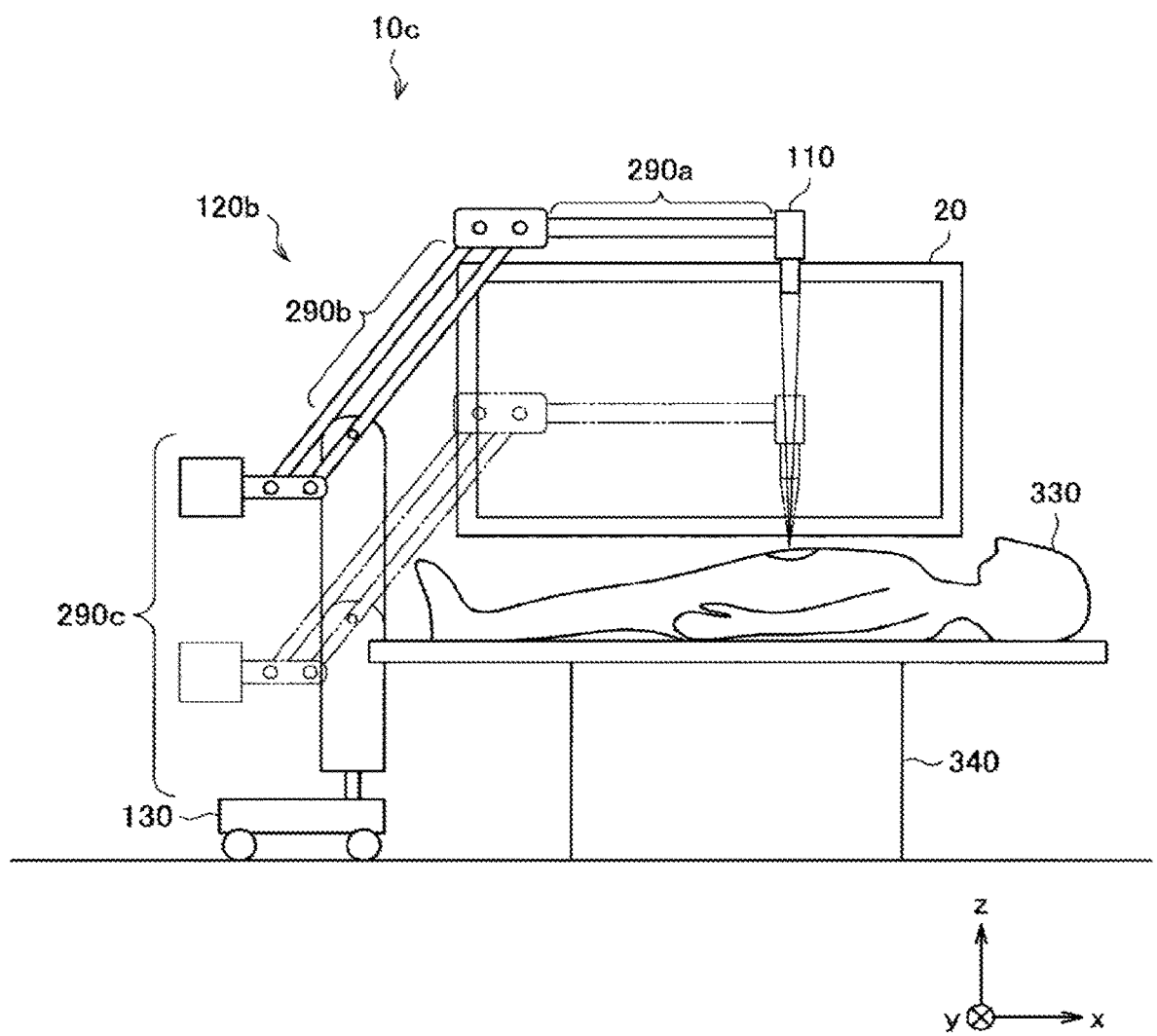
FIG. 15 is a diagram illustrating a configuration example of a microscope device according to a modification in which a prop unit is configured to have a greater length (T).

FIG. 15 is a diagram illustrating a configuration example of a microscope device according to a modification in which a prop unit is configured to have a greater length (T). FIG. 15 also illustrates the display device 20, and the patient 330 lying down on the operating table 340. Further, FIG. 15 illustrates the preferred attitude of a microscope device 10c according to the present modification in an operation at the seated position. Additionally, the microscope device according to the present modification is configured as described above in a similar way to the microscope device 10 according to the embodiment described above with reference to FIG. 9 except that the length (T) of the prop unit 290c is different. FIG. 15 thus simplifies the microscope device according to the present modification for the sake of simplicity. Further, FIG. 15 schematically overlays the microscope device 10 according to the above-described embodiment on the microscope device according to the present modification with a two-dot chain line for comparison.

As illustrated in FIG. 15, the microscope device 10c according to the present modification includes the microscope unit 110 for the magnified observation of an operative site of a patient, a support unit 120b that holds the microscope unit 110, and the base unit 130 that is connected to an end of the support unit 120b and supports the microscope unit 110 and the support unit 120b. Further, although not illustrated, the microscope device 10c also includes the control device 140 that controls the operation of the microscope device 10c similarly to the microscope device 10. The configurations and the functions of the microscope unit 110, the base unit 130, and the control device 140 are similar to the configurations and the functions of the respective components of the above-described microscope device 10, and will not be then described in detail.

The configuration and the function of the support unit 120b are also substantially similar to the configuration and the function of the support unit 120 of the microscope device 10. However, as described above, the prop unit 290c of the support unit 120b is configured to have greater length (T) than that of the prop unit 290c of the support unit 120.

Specifically, the display device 20 can be installed at a lower position than that of the above-described embodiments in the present modification. For example, the display device 20 can be installed to be positioned substantially in front of a surgeon in an operation at the seated position. The prop unit 290c is then configured to have such length that the microscope unit 110 can be disposed above display device 20 as illustrated even in an operation at the seated position, in which the microscope unit 110 is disposed at a lower position. Further, the first arm 290a is then kept substantially level. This is because the first arm 290a obstructs the least the view of a surgeon visually recognizing the display device 20 similarly to the above-described embodiments when the first arm 290a is kept substantially level. This configuration allows the surgeon to observe the display device 20 through the space between the patient 330 and the microscope unit 110 in an operation at the seated position. Accordingly, it is possible to prevent the microscope unit 110 and the support unit 120b from obstructing the view of the surgeon. Additionally, the microscope unit 110 is configured to have a longer focal distance and a longer WD that those of the above-described embodiments in the present modification because of this configuration.

Meanwhile, as the operating table 340 is higher, the position of the microscope unit 110 in the height direction is adjusted as appropriate to be higher in an operation at the standing position than the position in an operation at the seated position while the first arm 290a is kept substantially level. The microscope unit 110 is also thus disposed above the display device 20 in an operation at the standing position, and the microscope unit 110 and the support unit 120b do not obstruct the view of a surgeon.

The attitude of the support unit 120b is switched between operations at the seated position and operations at the standing position by changing the rotation angle $r_2$ of the second arm 290b with the prop unit 290c similarly to the above-described embodiments. Specifically, the attitude in operations at the seated position can be achieved by disposing the microscope device 10c such that the base unit 130 can be positioned relatively far from the operating table 340, and inclining the second arm 290b from the prop unit 290c at a relatively large angle (i.e., making the rotation angle $r_2$ relatively large). Meanwhile, the attitude in operations at the standing position can be achieved by disposing the microscope device 10c such that the base unit 130 can be positioned relatively close to the operating table 340, and inclining the second arm 290b from the prop unit 290c at a relatively small angle (i.e., making the rotation angle $r_2$ relatively small).

Here, the components closer to the distal-end side than the prop unit 290c of the support unit 120b of the microscope device 10c are similar to those of the support unit 120 of the microscope device 10 according to the above-described embodiment. That is, the components such as the counterweight 280 closer to the distal-end side than the prop unit 290c in the support unit 120b can be configured to be relatively small similarly the above-described embodiments. In this way, the height of the entire microscope device 10c is greater than that of the above-described embodiments with an increase in the length (T) of the prop unit 290c of the microscope device 10c. However, the width of the entire device can be favorably kept small similarly the above-described embodiments.

5-3-3. Design Idea of Support Unit

The configuration of the support unit 120b according to the present modification can also be designed on the basis of a substantially similar design idea to that of the above-described embodiments. It is, however, necessary to further increase the length (T) of the prop unit 290c, so that (Condition 1) above to (Condition 7) above are partially changed.

Specifically, the "conditions requested by the use modes" are not changed from those of the above-described embodiments. That is, the support unit 120b according to the present modification can be configured such that (Condition 1) above to (Condition 3) above are satisfied.

Meanwhile, speaking of the "conditions requested by the movable range and miniaturization," (Condition 4) above and (Condition 6) above are not changed from those of the above-described embodiments. Meanwhile, (Condition 5) above is changed. Specifically, a result of consideration of the present inventors reveals that is preferable to configure the support unit 120b such that (Condition 5') below and (Condition 6) above are satisfied, in order to achieve the relatively small microscope device 10c while satisfying the movable range shown in (Condition 4) above is satisfied.

$$H+V+T < \text{approximately 2600 (mm)} \quad \text{(Condition 5')}$$

Further, the "condition requested by the installation position" (i.e., (Condition 7) above) is not taken into consideration in the present modification. As described above when (Condition 7) is described, it is preferable for securing a clean area that the length (T) of the prop unit 290c be shorter than the height (B) of the operating table 340. However, even if the length (T) of the prop unit 290c is greater than the height (B) of the operating table 340, a clean area can be sufficiently secured by taking measures such as covering the prop unit 290c with a drape. Thus, to further improve the convenience of a surgeon, the upper limit of the length (T) of the prop unit 290c is not defined with the height (B) of the operating table 340 in the present modification.

In summary, the conditions for configuring the support unit 120b in the present modification are (Condition 1) above to (Condition 4) above, (Condition 5') above, and (Condition 6) above. The support unit 120b is configured in the present modification such that at least (Condition 1) above is satisfied. Further, 120b may be configured such that (Condition 2) above and (Condition 3) above are further satisfied. This allows the first arm 290a to be kept substantially level in an operation similarly to the above-described embodiments, and it is thus possible to more reliably secure the view of a surgeon and further improve the convenience of the surgeon. At this time, it is possible to keep the first arm 290a substantially level in both operations at the standing position and operations at the seated position, which can secure the working space of the surgeon regardless of the operation modes. Further, 120b may be configured such that (Condition 4) above, (Condition 5') above, and (Condition 6) above are further satisfied. This can miniaturize the microscope device 10c while securing the microscope unit 110 a sufficient movable range that can cover a variety of surgical procedures. Accordingly, the convenience of a surgeon can be further improved.

5-3-4. Specific Design Example of Support Unit

The present inventors have actually designed the configuration of the support unit 120b according to the present modification which can satisfy each of the above-described conditions similarly to the above-described embodiments. Here, a design result in a case where the support unit 120b is configured such that (Condition 1) above to (Condition 4) above, (Condition 5') above, and (Condition 6) above are all satisfied will be described as an example.

Specifically, the upper limit value of the length (V) of the second arm 290b can be decided from (Condition 2) above similarly to the above-described embodiments. Further, once the upper limit value of V is decided, the upper limit value of the length (H) of the first arm 290a can be decided from (Condition 1) above and the lower limit value of the length (T) of the prop unit 290c can be decided from (Condition 3) above. The specific values of H, V, and T are decided within the decided ranges of H, V, and T such that (Condition 4) above, (Condition 5') above, and (Condition 6) above are satisfied.

A result obtained by the present inventors actually designing the support unit 120b by setting the horizontal required arrival distance (WH) and the vertical required arrival distance (WV) in (Condition 4) above as WH=800 (mm) and WV=1600 (mm), and setting the maximum value $WD_{max}$ of the WD of the microscope unit 110 as $WD_{max}$=approximately 400 (mm) to approximately 600 (mm) in consideration of typical conditions (such as the height (sitting height) of a surgeon, the height of the operating table 340, and the installation position of the display device 20 in the height direction) for an operation reveals that the following relationship can be generally satisfied between the length (H) of the first arm 290a, the length (V) of the second arm 290b, and the length (T) of the prop unit 290c.

$H+V+T>$approximately 2000 (mm)

approximately 800 (mm)$<V<$approximately 1000 (mm)

approximately 600 (mm)$<H<$approximately 800 (mm)

approximately 800 (mm)$<T<$approximately 1000 (mm)

Additionally, the length (T) of the prop unit 290c is increased, and the position of the microscope unit 110 is relatively all the higher as compared with the microscope device 10 according to the above-described embodiments in the present modification. To dispose the microscope unit 110 at an appropriate position in an operation at the seated position, it is thus necessary to incline the second arm 290b to the prop unit 290c more considerably. Therefore, the value of the maximum value $r_{2max}$ of the rotation angle $r_2$ of the second arm 290b with the prop unit 290c can also be changed from that of the above-described embodiments in the present modification. A result of consideration of the present inventors reveals that it is preferable that the maximum value $r_{2max}$ of the rotation angle $r_2$ have a range of approximately $45°<r_{2max}<$approximately $65°$, in order to appropriately support operations at the seated position while configuring the support unit 120b such that (Condition 1) above to (Condition 4) above, (Condition 5') above, and (Condition 6) above are all satisfied.

Further, the microscope unit 110 is also configured in the present modification such that the length thereof in the optical axis direction (more strictly, the length from the connection portion of the first arm 290a and the microscope unit 110 to the lower end of the microscope unit 110) is, for example, approximately 200 mm or shorter. Even if the support unit 120b is configured such that the microscope unit 110 can be positioned above the display device 20 while the first arm 290a is kept substantially level, the microscope unit 110 having too large a size can prevent preferable observation on the display device 20. The configuration of the microscope unit 110 is made relatively small in this way in the present modification, thereby making it possible to more reliably secure the view of a surgeon.

5-3-5. Use Example of Microscope Device

Figure 16:
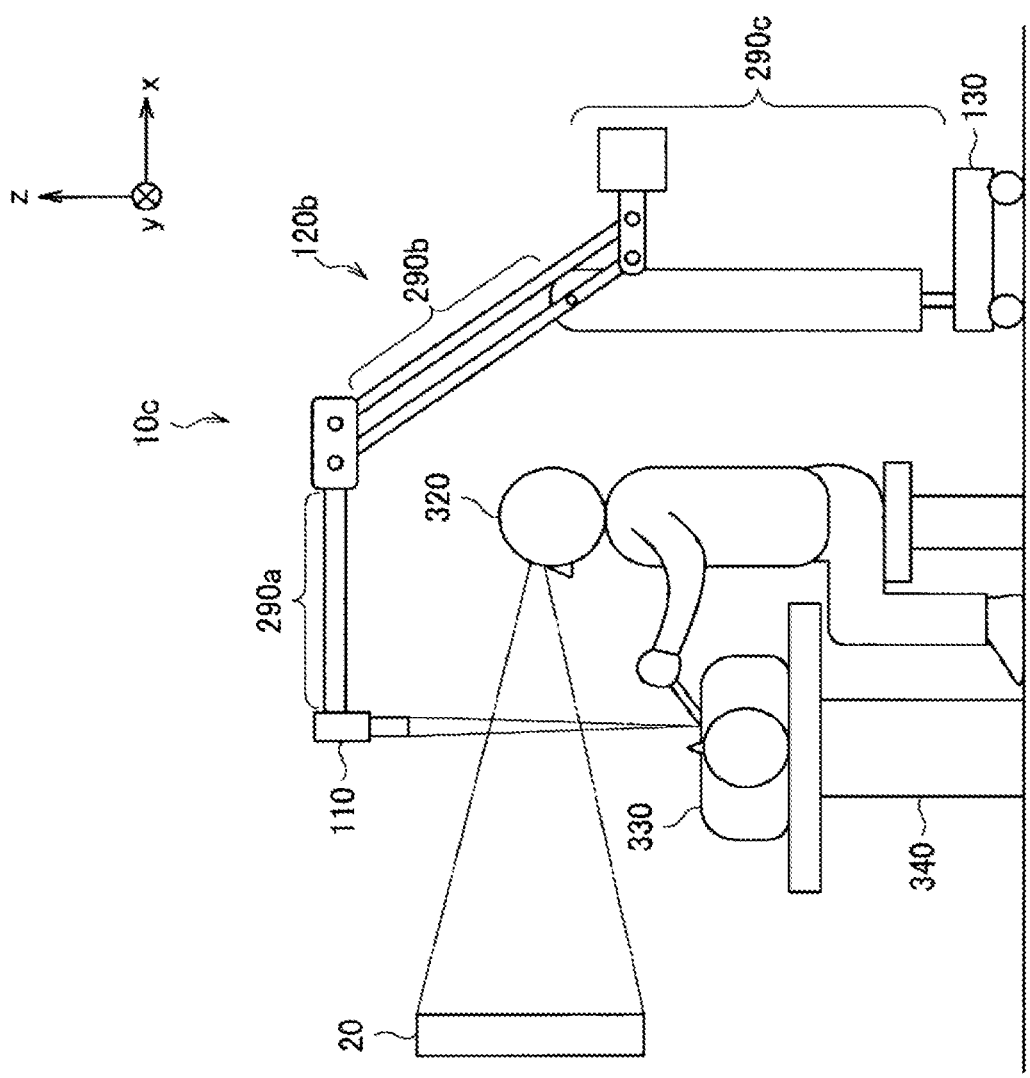
FIG. 16 is a diagram illustrating an operation using the microscope device according to the present modification at a seated position.

A use example of the microscope device 10c according to the present modification will be described with reference to FIG. 16. FIG. 16 is a diagram illustrating an operation using the microscope device 10c according to the present modification at the seated position.

FIG. 16 illustrates that the surgeon 320 uses the microscope device 10c to operate on the patient 330 lying down on the operating table 340 at the seated position. An image of an operative site of the patient 330 is captured by the microscope unit 110 of the microscope device 10c, and the captured image of the operative site is displayed on the display device 20 in an operation. The surgeon 320 performs an operation while observing the image of the operative site shown on the display device 20.

As illustrated, the surgeon 320 can come into the space under the first arm 290a, and perform an operation at the seated position by using the microscope device 10c according to the present modification, which namely means that the operation can be performed in the overhead style. The microscope unit 110 can be disposed at a higher position than the positon in the above-described embodiments in the present modification. Accordingly, a space into which the surgeon 320 comes is created under the first arm 290*a*, and enables such an operation in the overhead style. An operation in the overhead style eliminates the possibility that the microscope device 10*c* is installed such that the support unit 120*b* extends from the front of the surgeon 320 or a side of the surgeon 320 toward the surgeon 320. The space in front of the eyes of the surgeon 320 can be secured more.

The following describes an operation procedure of the microscope device 10*c* in an operation at the seated position. Additionally, the operation procedure of the microscope device 10*c* in an operation at the seated position is substantially similar to the operation procedure of the microscope device 10 described in (4-2. Use Example in Operations at Seated Position) above. What is common thereto will not be thus described in detail.

First, when an operation begins, the entire microscope device 10 is moved close to the operating table 340 by using the casters. The microscope device 10*c* is then installed at a position farther from the operating table 340 than the position in operations at the standing position.

Grasping a grip unit of the microscope unit 110, the surgeon 320 then pushes down the operation mode change SW 153 to release the brakes provided to the first rotary shaft 210 to the sixth rotary shaft 260 and set the free operation mode, in which the microscope unit 110 can be namely moved freely. While observing the image that is captured by the microscope unit 110 and displayed on the display device 20, the surgeon 320 moves the microscope unit 110 to allow the microscope unit 110 to bring the operative site into view. The surgeon 320 then releases the operation mode change SW 153 (i.e., changes the operation mode into the fixation mode) to fix the attitudes of the microscope unit 110 and the support unit 120*b*.

Here, the microscope device 10*c* is configured in the present modification such that the prop unit 290*c* of the support unit 120*b* has greater length (T), so that it is possible to dispose the microscope unit 110 at a higher position than the position in the above-described embodiments. Specifically, it is possible to dispose the microscope unit 110 above the display device 20. Further, at this time, the microscope device 10*c* is configured such that the length (V) of the second arm 290*b* is greater than the length (H) of the first arm 290*a*. Accordingly, if the microscope device 10*c* is disposed at a position relatively far from the operating table 340 and the attitude of the support unit 120*b* is adjusted such that the second arm 290*b* is inclined toward the operating table 340, it is possible to dispose the microscope unit 110 at the above-described higher position while keeping the first arm 290*a* substantially level.

The surgeon 320 operates the zoom SW 151 and the focus SW 152 once the attitudes of the microscope unit 110 and the support unit 120*b* are fixed, and adjusts the magnification and the focal distance of an image captured by the microscope unit 110. As described above, the microscope unit 110 is configured in the present modification to have a relatively long focal distance, so that it is possible to acquire a clear image that has an operative site in focus even if the microscope unit 110 is disposed at the above-described higher position.

The surgeon 320 then sits down in the space under the first arm 290*a*, and begins treatment while observing an image of the display device 20 through the space between an operative site of the patient 330 and the microscope unit 110. That is, the surgeon 320 begins an operation in the overhead style. At this time, it is possible in the present modification to dispose the microscope unit 110 above the display device 20 as described above while keeping the first arm 290*a* substantially level. The view of the surgeon 320 is not thus obstructed by the microscope unit 110, but it is possible to smoothly perform an operation.

The use example of the microscope device 10 in operations at the seated position has been described above with reference to FIG. 11. Additionally, in a case where an operation is performed at the standing position, the microscope device 10*c* is installed at a position closer to the operating table 340, and the rotation angle $r_2$ of the second arm 290*b* with the prop unit 290*c* is made smaller to dispose the microscope unit 110 at a higher position as compared with a case where an operation is performed at the seated position. This makes it possible to dispose the microscope unit 110 at a position appropriate for an operation at the standing position in accordance with the higher position of the operating table 340 than the position in an operation at the seated position. At this time, the first arm 290*a* can also be kept substantially level, and the microscope unit 110 can be disposed above the display device 20. Accordingly, it is possible to prevent the microscope unit 110 from obstructing the view of the surgeon 320.

Here, as described in (1. Background Where the Present Disclosure Has Been Conceived) above, the optical microscope device 810 is made on the assumption of use in the overhead style, and it is not always appropriate for the configuration of the electronic imaging microscope device to directly apply the configuration of the support unit 803 of the optical microscope device 810 to the electronic imaging microscope device. Specifically, the microscope unit of the electronic imaging microscope device can be miniaturized, so that it is also possible to miniaturize the configuration of the entire device. It is thus possible to configure the smaller microscope device 10 that is not made on the assumption of use in the overhead style unlike the above-described embodiments.

Meanwhile, there can be, in general, needs for operations in the overhead style as operations with the microscope device. This is because, as described above, in a case where an operation is performed in the overhead style, no support unit exists in front of a surgeon or on a side of a surgeon, so that the view and working space of the surgeon can be secured more. That is, it is not always unfavorable that the electronic imaging microscope device be used in the overhead style. In other words, if the electronic imaging microscope device is configured even in consideration of use in the overhead style, there is the probability that a smaller microscope device which can further improve the convenience of a surgeon is achieved.

The microscope device 10*c* according to the present modification can cover operations in the overhead style in this way when operations at the seated position are performed, while keeping the size of the entire device smaller than that of the optical microscope device 810. Specifically, the microscope device 10*c* includes the electronic imaging microscope unit 110, so that the WD of the microscope unit 110 can be greater than that of the optical microscope unit 801. It is thus possible to configure the microscope device 10*c* such that the microscope unit 110 can be positioned above the display device 20 when used in the overhead style, namely the microscope unit 110 is not positioned in front of the eyes of a surgeon. The microscope unit 110 does not obstruct the view of a surgeon in the configuration even when used in the overhead style. Further, even if the microscope device 10c is configured in this way, the size of the microscope unit 110 can be smaller than that of the optical microscope unit 801, and the support unit 120b and the counterweight can also be miniaturized. Accordingly, the size of the entire microscope device 10c can be smaller than that of the optical microscope device 810. The above-described disposition of the microscope unit 110 is achieved especially in the present modification by increasing the length (T) of the prop unit 290c without changing the components closer to the distal-end side than the prop unit 290c in the microscope device 10 according to the above-described embodiments, so that the support unit 120b and the counterweight can be favorably kept smaller.

In this way, the microscope device 10c according to the present modification can improve the degree of freedom regarding the disposition of the microscope device 10c, namely the degree of freedom regarding the use modes in operations, while achieving the miniaturization of the entire device, and the convenience of the surgeon 320 can be further improved. Favorably, operations with the microscope device 10c according to the present modification in the overhead style can be limited to operations such as brain surgery which are performed at the seated position. This is because the use of the microscope device 10c in the overhead style in an operation at the standing position causes the support unit 120b to be relatively large even if the microscope unit 110 can be miniaturized, and it can be difficult to benefit from the advantage that the entire device can be smaller than the optical microscope device 810. The microscope device 10c can be thus installed not in the overhead style, but in front of the surgeon 320 or on a side of the surgeon 320, for example, similarly to the use mode illustrated in FIG. 10 in an operation at the standing position in the present modification.

5-4. Modification in Which Image Vibration Reduction Mechanism is Included

The above-described microscope devices 10, and 10a to 10c may include an image vibration reduction mechanism that reduces the vibration of an image captured by the microscope unit 110. If such an image vibration reduction mechanism is included, it is possible to acquire a more stable image of an operative site, and more smoothly perform an operation.

Specifically, the microscope devices 10, and 10a to 10c can include a mechanical vibration reduction mechanism that can be provided to each of the first rotary shaft 210 to the sixth rotary shaft 260 of the support units 120, 120a, and 120b for the purpose of reducing the vibration of the microscope unit 110, and/or an image vibration correction mechanism that corrects the vibration of an image captured in a case where the microscope unit 110 is vibrated, as the image vibration reduction mechanism.

First, the mechanical vibration reduction mechanism will be described. The mechanical vibration reduction mechanism is, for example, a dynamic vibration reducer, and includes a vibration reduction member such as a damper. The mechanical vibration reduction mechanism can reduce the vibration of each rotary shaft.

Figure 17:
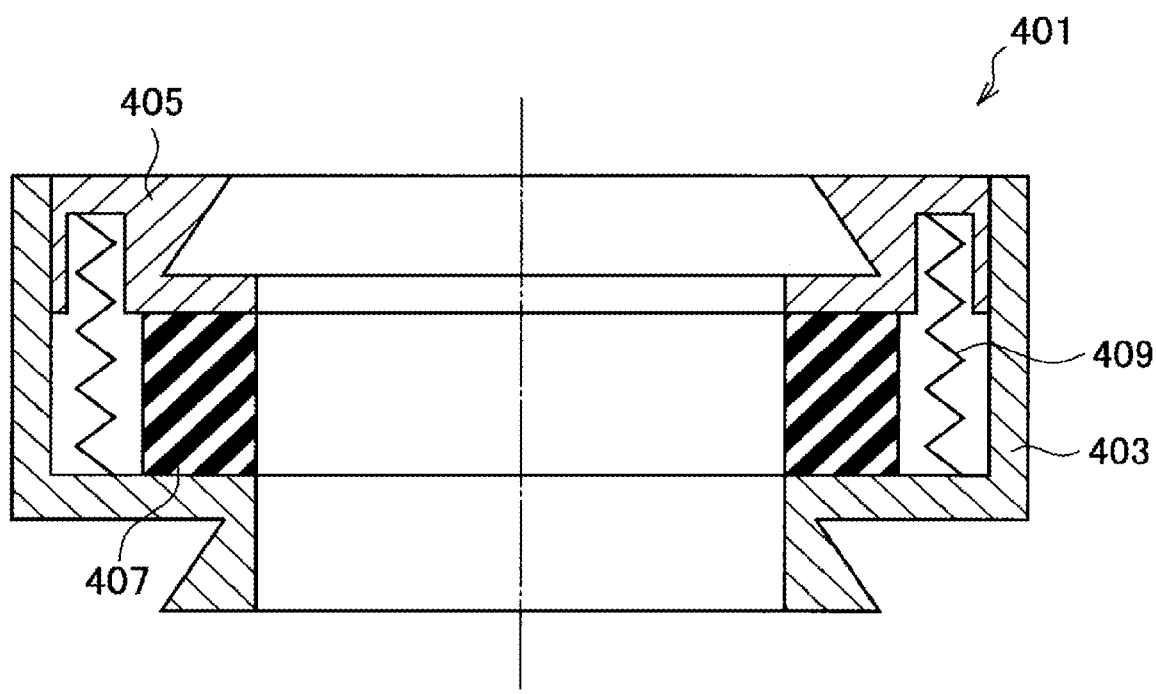
FIG. 17 is a diagram illustrating a configuration example of a mechanical vibration reduction mechanism that can be provided to each rotary shaft.

Some specific configuration examples of the mechanical vibration reduction mechanism will be described with reference to FIGS. 17 and 18. FIG. 17 is a diagram illustrating a configuration example of a mechanical vibration reduction mechanism that can be provided to each rotary shaft. FIG. 17 illustrates that a vibration reduction mechanism 401 is provided between a cylindrical first member 403 and second member 405 when these members are connected, and has a function of reducing the vibration transmitted between these members. Specifically, the second member 405 (weight-side member 405) is fitted into the cylindrical first member 403 (vibration reduction target member 403) that is a vibration reduction target such that the second member 405 can slide in the axial direction (up-down direction in the figure). The second member 405 and the cylindrical first member 403 are hereby connected in this configuration example. At this time, a viscoelastic member 407 and a spring 409 are provided between the vibration reduction target member 403 and the weight-side member 405 as viscous resistance elements. The vibration reduction mechanism 401 is a dynamic vibration reducer including the viscoelastic member 407 and the spring 409. Additionally, the viscoelastic member 407 includes a rubber member such as silicone rubber or urethane rubber, and has both a mechanical property and a property as a spring element.

The viscoelastic member 407 and the spring 409 have a function of expanding and contracting in the axial direction in accordance with the vibration of the vibration reduction target member 403 and the weight-side member 405 to attenuate this vibration. The natural frequency of the vibration reduction mechanism 401 is decided in accordance with the characteristics of the viscoelastic member 407 and the spring 409. In a case where this natural frequency agrees with the natural frequencies of the support units 120, 120a, and 120b that are vibration reduction targets, the highest vibration reduction effects can be attained. The vibration reduction mechanism 401 may thus exchange the viscoelastic member 407 and the spring 409 with what have different characteristics. This allows the vibration reduction mechanism 401 to be configured as appropriate in accordance with the configurations of the support units 120, 120a, and 120b such that the natural frequency of the vibration reduction mechanism 401 substantially agrees with the natural frequencies of the support units 120, 120a, and 120b, and the high vibration reduction effects can be attained.

Figure 18:
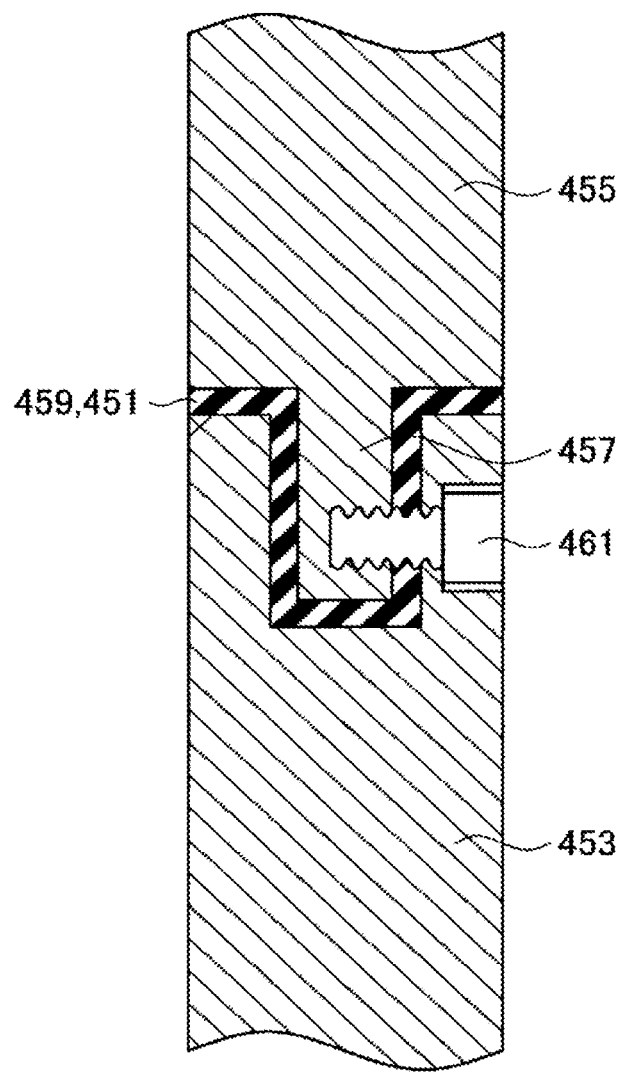
FIG. 18 is a diagram illustrating another configuration example of the vibration reduction mechanism that can be provided to each rotary shaft.

Further, FIG. 18 is a diagram illustrating another configuration example of the vibration reduction mechanism that can be provided to each rotary shaft. FIG. 18 illustrates that a vibration reduction mechanism 451 is provided between a first member 453 and second member 455 each of which is shaped substantially like a stick when these members are connected, and has a function of reducing the vibration transmitted between these members. Specifically, a concave strike 459 is provided to the connection end of the first member 453 in this configuration example. The concave strike 459 includes an elastic member such as rubber that can absorb vibration. Further, a shaft 457 is provided to the connection end of the second member 455. The shaft 457 is thinner in external diameter than the other portions. The first member 453, the strike 459, and the shaft 457 are then fixed by a screw 461 with the shaft 457 of this second member 455 inserted into the concave part of the strike 459, thereby connecting the first member 453 to the second member 455. This strike 459 can constitute the vibration reduction mechanism 451 that absorbs vibration. Additionally, there may be then provided an elastic member such as rubber (not illustrated) that can absorb vibration between the screw 461 and the first member 453, and the vibration reduction mechanism 451 may include the strike 459 and the elastic member.

As illustrated, the strike 459 has a concave shape, so that the strike 459 can favorably reduce all vibration in the triaxial direction. In this way, the vibration reduction mechanism 451 can more effectively suppress the transmission of the vibration generated at any one of the first member 453 and the second member 455 to the other.

Some configuration examples of the mechanical vibration reduction mechanism that can be provided to each rotary shaft of the support units 120, 120a, and 120b have been described above with reference to FIGS. 17 and 18. Additionally, a variety of known vibration reduction mechanisms can also be used as the vibration reduction mechanism in addition to what is illustrated.

Next, the image vibration correction mechanism will be described. Any of an electronic correction mechanism and an optical correction mechanism can be used as the image vibration correction mechanism. The electronic correction mechanism detects the vibration state of the imaging unit 111, and corrects the vibration of an image by correcting a positon at which observation light of each pixel of an image sensor of the imaging unit 111 is obtained, on the basis of the detected vibration state when performing image processing on an image signal acquired by the image sensor. Meanwhile, the optical correction mechanism detects the vibration state of the imaging unit 111, and adjusts the light-receiving positon of observation light on an image sensor by moving the position of the optical system (such as a lens) of the imaging unit 111 or the position of the image sensor and corrects the vibration of an image on the basis of the detected vibration state. Additionally, the vibration state of the imaging unit 111 may be detected by providing a vibration sensor to the microscope unit 110, or buffering a captured image for a certain period of time and comparing the latest image with the most recent image.

A variety of image vibration correction mechanisms generally known in the technical field of hand-shake correction for imaging devices such as digital cameras can be used as these image vibration correction mechanisms. The detailed description thereof will not be then made.

The image vibration reduction mechanisms that can be mounted on the microscope devices 10, and 10a to 10c have been described above. Here, as described above, the microscope device 10c according to the modification in which the prop unit is configured to have greater length (T) is configured such that the microscope unit 110 is disposed at a higher position than those of the other microscope devices 10, 10a, and 10b, and the WD thereof is longer. There is thus the possibility that the vibration of the microscope unit 110 of the microscope device 10c has greater influence on a captured image than those of the other microscope devices 10, 10a, and 10b. The above-described image vibration reduction mechanism provided to the microscope device 10c can thus more eminently attain the advantageous effect that a stable image is acquired.

6. Supplemental Information

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A surgical microscope device including:

a microscope unit configured to image an operative site of a patient on an operating table, and output an image signal; and a support unit configured to support the microscope unit at a distal end, in which in a case where it is assumed that the support unit includes a first arm, a second arm, and a prop unit in an order from a distal-end side, the second arm supporting a proximal end of the first arm at a distal end rotatably around a first rotation axis orthogonal to a vertical direction and a front-back direction, the prop unit extending from a floor substantially in the vertical direction and supporting a proximal end of the second arm at a distal end rotatably around a second rotation axis orthogonal to the vertical direction and the front-back direction, the support unit is configured such that a length of the second arm as a length between the first rotation axis and the second rotation axis is greater than a length of the first arm as a length between the first rotation axis and an optical axis of the microscope unit disposed to have the optical axis substantially vertical.

(2)

The surgical microscope device according to (1), in which in a case where the length of the second arm is represented as V, a rotation angle of the second arm with the prop unit is represented as $r_2$, a height of the microscope unit from the floor in an operation at a standing position is represented as $Z_1$, and a height of the microscope unit from the floor in an operation at a seated position is represented as $Z_2$, the length V, the rotation angle $r_2$, the height $Z_1$, and the height $Z_2$ satisfy a relationship represented as $Z_1-Z_2<V(1-\cos(r_2))$.

(3)

The surgical microscope device according to (2), in which the length V, the rotation angle $r_2$, the height $Z_1$, and the height $Z_2$ satisfy a relationship represented as $200 \text{ (mm)} < V(1-\cos(r_2))$.

(4)

The surgical microscope device according to any one of (1) to (3), in which in a case where a length of the prop unit is represented as T, a rotation angle of the second arm with the prop unit is represented as $r_2$, and a height of the microscope unit from the floor in an operation at a seated position is represented as $Z_2$, the length V, the rotation angle $r_2$, and the height $Z_2$ satisfy a relationship represented as $Z_2 > V\cos(r_2)+T$.

(5)

The surgical microscope device according to any one of (1) to (4), in which the support unit is configured such that the microscope unit passes through a position in a space that has a distance of approximately 800 (mm) from the prop unit in a horizontal direction and a distance of approximately 1600 (mm) from the floor in the vertical direction.

(6)

The surgical microscope device according to (5), in which the support unit is configured such that a total length of the length of the first arm, the length of the second arm, and a length of the prop unit is less than 2500 (mm).

(7)

The surgical microscope device according to (5) or (6), in which in a case where a rotation angle of the first arm with the second arm is represented as $r_1$, and a rotation angle of the second arm with the prop unit is represented as $r_2$, the rotation angle $r_1$ and the rotation angle $r_2$ satisfy a relationship represented as approximately $130° < r_1 + r_2 <$ approximately $180°$.

(8)

The surgical microscope device according to any one of (1) to (7), in which the support unit is configured such that a length of the prop unit is shorter than a height of the operating table.

(9)

The surgical microscope device according to (8), in which the length of the prop unit is shorter than 800 (mm).

(10)

The surgical microscope device according to (5), in which a length T of the prop unit satisfies a relationship represented as approximately 800 (mm)$<$T$<$approximately 1000 (mm).

(11)

The surgical microscope device according to any one of (10), in which a maximum value $WD_{max}$ of a working distance of the microscope unit satisfies a relationship represented as approximately 400 (mm)$\leq WD_{max} \leq$ approximately 600 (mm).

(12)

The surgical microscope device according to any one of (1) to (11), in which the support unit is configured such that a total length of the length of the first arm, the length of the second arm, and a length of the prop unit is greater than 2000 (mm).

(13)

The surgical microscope device according to any one of (1) to (12), in which the support unit is configured as a balance arm.

(14)

The surgical microscope device according to any one of (1) to (13), in which the second arm corresponds to a parallelogram link mechanism included in the support unit.

(15)

The surgical microscope device according to any one of (1) to (14), in which the support unit includes a rotary shaft at a position corresponding to a connection portion of the second arm and the prop unit, the rotary shaft supporting the second arm rotatably around a rotation axis parallel to an extending direction of the second arm.

(16)

The surgical microscope device according to any one of (1) to (15), in which an electrical unit is mounted on a top of a base unit configured to support a proximal end of the support unit, the electrical unit executing signal processing in the surgical microscope device, and the proximal end of the support unit is connected to a front side with respect to the electrical unit on the top of the base unit.

(17)

The surgical microscope device according to (16), in which the electrical unit is configured to be higher on a back side than on a front side on the top of the base unit.

(18)

A surgical microscope system including:

a microscope device including a microscope unit configured to image an operative site of a patient on an operating table and output an image signal, and a support unit configured to support the microscope unit at a distal end; and a display device configured to display an image based on the image signal, in which in a case where it is assumed that the support unit includes a first arm, a second arm, and a prop unit in an order from a distal-end side, the second arm supporting a proximal end of the first arm at a distal end rotatably around a first rotation axis orthogonal to a vertical direction and a front-back direction, the prop unit extending from a floor substantially in the vertical direction and supporting a proximal end of the second arm at a distal end rotatably around a second rotation axis orthogonal to the vertical direction and the front-back direction, the support unit is configured such that a length of the second arm as a length between the first rotation axis and the second rotation axis is greater than a length of the first arm as a length between the first rotation axis and an optical axis of the microscope unit disposed to have the optical axis substantially vertical.

REFERENCE SIGNS LIST 1 microscope system
10, 710, 810 microscope device
20, 760 display device
110, 701, 801 microscope unit
120, 703, 803 support unit (arm unit)
130 705, 805 base unit
131 stand
132 caster
140 control device
210 first rotary shaft
220 second rotary shaft
230 third rotary shaft
240 fourth rotary shaft (parallelogram link mechanism)
250 fifth rotary shaft
260 sixth rotary shaft
241, 242, 243, 244 arm
245, 246, 247, 248 joint unit
271 first arm unit
272 second arm unit
273 third arm unit
274 fourth arm unit
290a, 707a, 807a first arm
290b, 707b, 807b second arm
290c, 707c, 807c prop unit
320, 720, 820 surgeon
330, 730, 830 patient
340, 740, 840 operating table

The invention claimed is:

1. A surgical microscope device comprising:

a microscope configured to image an operative site of a patient on an operating table, and output an image signal; and a support configured to support the microscope at a distal end, wherein the support includes a first arm, a second arm, and a prop in an order from a distal-end side, the second arm supporting a proximal end of the first arm at a distal end rotatably around a first rotation axis orthogonal to a vertical direction and a front-back direction, the prop extending from a floor substantially in the vertical direction and supporting a proximal end of the second arm at a distal end rotatably around a second rotation axis orthogonal to the vertical direction and the front-back direction, the support is configured such that a length of the second arm as a length between the first rotation axis and the second rotation axis is greater than a length of the first arm as a length between the first rotation axis and an optical axis of the microscope disposed to have the optical axis substantially vertical, and wherein the support is configured such that 200 (mm)<V $(1-\cos(r_{2max}))$, where the length of the second arm is represented as V and a maximum value of a rotation angle of the second arm away from a vertical direction is represented as $r_{2max}$.

2. The surgical microscope device according to claim 1, wherein
the support is configured such that a length of the prop is shorter than a height of the operating table.

3. The surgical microscope device according to claim 2, wherein
the length of the prop is shorter than 800 (mm).

4. The surgical microscope device according to claim 1, wherein
the support is configured such that a total length of the length of the first arm, the length of the second arm, and a length of the prop is greater than 2000 (mm).

5. The surgical microscope device according to claim 1, wherein
the support is configured as a balance arm.

6. The surgical microscope device according to claim 1, wherein
the second arm corresponds to a parallelogram link mechanism included in the support.

7. The surgical microscope device according to claim 1, wherein
the support includes a rotary shaft at a position corresponding to a connection portion of the second arm and the prop, the rotary shaft supporting the second arm rotatably around a rotation axis parallel to an extending direction of the second arm.

8. The surgical microscope device according to claim 1, wherein
processing circuitry is mounted on a top of a base configured to support a proximal end of the support unit, the processing circuitry executing signal processing in the surgical microscope device, and
the proximal end of the support is connected to a front side with respect to the electrical unit on the top of the base.

9. The surgical microscope device according to claim 8, wherein
the processing circuitry is configured to be higher on a back side than on a front side on the top of the base.

10. A surgical microscope system comprising:
a microscope configured to image an operative site of a patient on an operating table and output an image signal, and a support configured to support the microscope at a distal end; and
a display configured to display an image based on the image signal, wherein
the support includes a first arm, a second arm, and a prop in an order from a distal-end side, the second arm supporting a proximal end of the first arm at a distal end rotatably around a first rotation axis orthogonal to a vertical direction and a front-back direction, the prop extending from a floor substantially in the vertical direction and supporting a proximal end of the second arm at a distal end rotatably around a second rotation axis orthogonal to the vertical direction and the front-back direction,
the support is configured such that a length of the second arm as a length between the first rotation axis and the second rotation axis is greater than a length of the first arm as a length between the first rotation axis and an optical axis of the microscope disposed to have the optical axis substantially vertical, and
wherein the support is configured such that 200 (mm)<V $(1-\cos(r_{2max}))$, where the length of the second arm is represented as V and a maximum value of a rotation angle of the second arm away from a vertical direction is represented as $r_{2max}$.

* * * * *